United States Patent
Best et al.

(10) Patent No.: US 10,927,325 B2
(45) Date of Patent: Feb. 23, 2021

(54) DETERGENT COMPOSITIONS

(71) Applicant: Conopco, Inc., Englewood Cliffs, NJ (US)

(72) Inventors: Jonathan Best, Frodsham (GB); Andrew Thomas Cook, Liverpool (GB); Thomas Eisele, Planegg (DE); Michael Hoesl, Planegg (DE); Claudia Jakob, Planegg (DE); Helge Jochens, Planegg (DE); Andreas Kohl, Planegg (DE); Panagiotis Kotsakis, Athens (GR); Dietmar Andreas Lang, Liverpool (GB); Timothy O'Connell, Planegg (DE); Neil James Parry, Tarporley (GB); Ilaria Sambi, Liverpool (GB); Frank Wallrapp, Planegg (DE)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/496,627

(22) PCT Filed: Mar. 8, 2018

(86) PCT No.: PCT/EP2018/055759
§ 371 (c)(1),
(2) Date: Sep. 23, 2019

(87) PCT Pub. No.: WO2018/172090
PCT Pub. Date: Sep. 27, 2018

(65) Prior Publication Data
US 2020/0369988 A1    Nov. 26, 2020

(30) Foreign Application Priority Data

Mar. 24, 2017  (EP) ..................... 17162871

(51) Int. Cl.
| | | |
|---|---|---|
| *C11D 3/386* | (2006.01) | |
| *C11D 3/40* | (2006.01) | |
| *C11D 3/34* | (2006.01) | |
| *C11D 11/00* | (2006.01) | |

(52) U.S. Cl.
CPC .......... *C11D 3/38645* (2013.01); *C11D 3/349* (2013.01); *C11D 3/40* (2013.01); *C11D 11/0017* (2013.01)

(58) Field of Classification Search
None
See application file for complete search history.

(56) References Cited

U.S. PATENT DOCUMENTS

| 2005/0070003 A1 | 3/2005 | Schulein et al. |
| 2016/0137956 A1 | 5/2016 | Hayward et al. |

FOREIGN PATENT DOCUMENTS

| WO | WO2011117728 | 9/2011 |
| WO | WO2012059363 | 5/2012 |

OTHER PUBLICATIONS

IPRP2 in PCTEP2018055759; dated Feb. 27, 2019; World Intellectual Property Org. (WIPO).
Search Report and Written Opinion in PCTEP2018055759.
Search Report and Written Opinion in EP17162871; dated Sep. 26, 2017.
Needleman et al.; A General Method Applicable to the Search for Similiarities in the Amino Acid Sequence of Two Proteins; J. Mol. Biol.; 1970; pp. 443-453; vol. 48.
Rice et al.; EMBOSS: The European Molecular Biology Open Software Suite; Trends Genet. ; 2000; 16 276-277; 16.

*Primary Examiner* — Suzanne M Noakes
*Assistant Examiner* — Jae W Lee
(74) *Attorney, Agent, or Firm* — Greenberg Traurig, LLP

(57) ABSTRACT

The invention relates to a detergent composition comprising: —(a) from 0.0001 to 1 wt. %, preferably from 0.0001 to 0.1 wt. %, more preferably from 0.0001 to 0.01 wt. %, most preferably from 0.0005 to 0.001 wt. % of a shading dye; and, (b) from 0.0001 to 10 wt. %, preferably from 0.0005 to 8 wt. %, more preferably from 0.001 to 5 wt. %, most preferably from 0.002 to 0.2 wt. % of a cellulase selected from any sequence with a sequence identity of at least 80%, preferably at least 85%, further preferred at least 90%, GO even more preferred at least 92%, also preferred at least 95%, particularly preferred at least 98% and most preferred at least 99% to SEQ ID NO: 11, SEQ ID NO: 13, SEQ ID NO: 15 or SEQ ID NO: 17.

8 Claims, 7 Drawing Sheets
Specification includes a Sequence Listing.

Figure 10 – AV 50
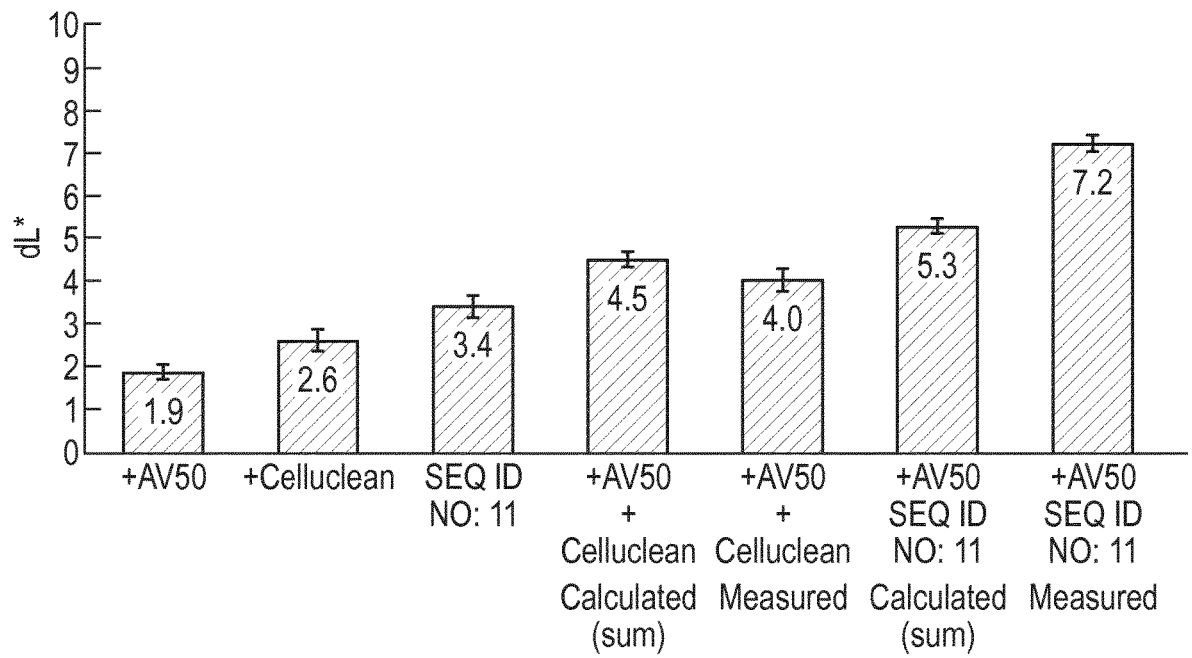
Figure 11
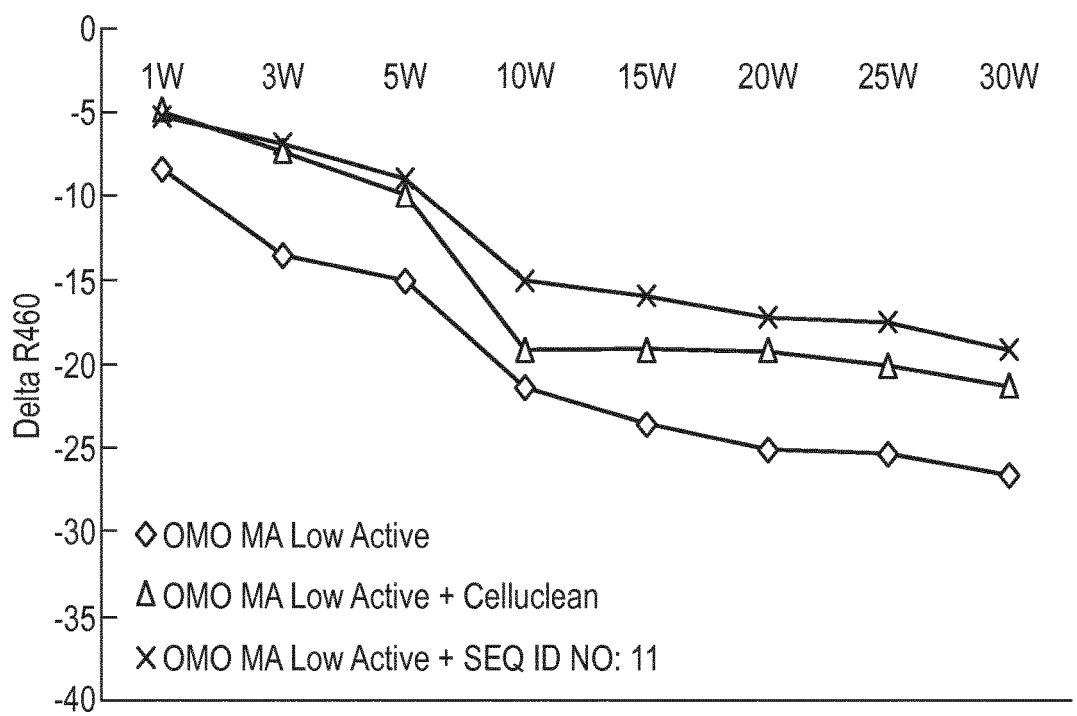

SEQUENCE LISTING

```
<160> NUMBER OF SEQ ID NOS: 24

<210> SEQ ID NO 1
<211> LENGTH: 204
<212> TYPE: PRT
<213> ORGANISM: Myceliophthora thermophila
<220> FEATURE:
<223> OTHER INFORMATION: cellulase

<400> SEQUENCE: 1

Gly Ser Gly Gln Thr Thr Arg Tyr Trp Asp Cys Cys Lys Pro Ser Cys
1               5                   10                  15

Ala Trp Pro Gly Lys Gly Pro Ser Ser Pro Val Gln Ala Cys Asp Lys
            20                  25                  30
```

```
Asn Asp Asn Pro Leu Asn Asp Gly Gly Ser Thr Arg Ser Gly Cys Asp
        35                  40                  45

Ala Gly Gly Ser Ala Tyr Met Cys Ser Ser Gln Ser Pro Trp Ala Val
 50                  55                  60

Ser Asp Glu Leu Ser Tyr Gly Trp Ala Ala Val Lys Leu Ala Gly Ser
 65                  70                  75                  80

Ser Glu Ser Gln Trp Cys Cys Ala Cys Tyr Glu Leu Thr Phe Thr Ser
                 85                  90                  95

Gly Pro Val Ala Gly Lys Lys Met Ile Val Gln Ala Thr Asn Thr Gly
                100                 105                 110

Gly Asp Leu Gly Asp Asn His Phe Asp Leu Ala Ile Pro Gly Gly Gly
        115                 120                 125

Val Gly Ile Phe Asn Ala Cys Thr Asp Gln Tyr Gly Ala Pro Pro Asn
    130                 135                 140

Gly Trp Gly Asp Arg Tyr Gly Gly Ile His Ser Lys Glu Glu Cys Glu
145                 150                 155                 160

Ser Phe Pro Glu Ala Leu Lys Pro Gly Cys Asn Trp Arg Phe Asp Trp
                165                 170                 175

Phe Gln Asn Ala Asp Asn Pro Ser Val Thr Phe Gln Gly Val Ala Cys
        180                 185                 190

Pro Ser Glu Leu Thr Ser Lys Ser Gly Cys Ser Arg
        195                 200
```

```
<210> SEQ ID NO 2
<211> LENGTH: 612
<212> TYPE: DNA
<213> ORGANISM: Myceliophthora thermophila
<220> FEATURE:
<223> OTHER INFORMATION: cellulase

<400> SEQUENCE: 2
ggcagcggcc agacgacccg gtactgggac tgctgcaagc cgagctgcgc ctggcccggc      60
aagggcccct cgtctccggt gcaggcctgc gacaagaacg acaacccgct caacgacggc     120
ggctccaccc ggtccggctg cgacgcgggc ggcagcgcct acatgtgctc ctcccagagc     180
ccctgggccg tcagcgacga gctgtcgtac ggctgggcgg ccgtcaagct cgccggcagc     240
tccgagtcgc agtggtgctg cgcctgctac gagctgacct tcaccagcgg gccggtcgcg     300
ggcaagaaga tgattgtgca ggcgaccaac accggtggcg acctgggcga caaccacttt     360
gacctggcca tccccggtgg cggtgtcggt attttcaacg cctgcaccga ccagtacggc     420
gctcccccga acggctgggg cgaccgctac ggcggcatcc attccaagga agagtgcgaa     480
tccttcccgg aggccctcaa gcccggctgc aactggcgct tcgactggtt ccaaaacgcc     540
gacaacccgt cggtcaccct tccaggaggtg gcctgcccgt cggagctcac gtccaagagc     600
ggctgctccc gt                                                          612
```

```
<210> SEQ ID NO 3
<211> LENGTH: 137
<212> TYPE: PRT
<213> ORGANISM: Streptomyces clavuligerus
<220> FEATURE:
<223> OTHER INFORMATION: CBM

<400> SEQUENCE: 3

Ala Asp Ala Leu Pro Ala Asp Arg Ala Pro Arg Ala Ala Val Leu Glu
 1               5                  10                  15
```

```
Ala Glu Asp Ala Thr Ile Ser Gln Gly Ala Val Glu Ser Asn His Arg
            20                  25                  30

Gly Tyr Thr Gly Arg Gly Phe Val Asn Tyr Asp Asn Leu Thr Gly Ser
        35                  40                  45

Ser Val Glu Trp Thr Val Arg Ala Asp Lys Ala Gly Thr Thr Pro Leu
    50                  55                  60

Thr Leu Arg Phe Ala Asn Gly Thr Thr Val Asn Arg Pro Met Thr Ile
65                  70                  75                  80

Ser Val Asn Gly Thr Pro Ala Leu Thr Gly Arg Ser Phe Pro Gly Asn
                85                  90                  95

Gly Ser Trp Thr Ser Trp Gln Thr Ala Asn Leu Asp Val Pro Leu Arg
            100                 105                 110

Glu Gly Asp Asn Thr Ile Arg Ala Thr Ala Thr Thr Ala Asn Gly Gly
            115                 120                 125

Pro Asn Val Asp Ser Leu Thr Val Pro
        130                 135
```

<210> SEQ ID NO 4
<211> LENGTH: 411
<212> TYPE: DNA
<213> ORGANISM: Streptomyces clavuligerus
<220> FEATURE:
<223> OTHER INFORMATION: CBM

<400> SEQUENCE: 4

```
gcggacgccc tccccgcgga ccgcgccccc cgggccgccg tgctcgaggc cgaggacgcg    60
accatctccc agggcgcggt cgagtccaac caccgcggct acaccggccg gggcttcgtc   120
aactacgaca acctcaccgg cagcagtgtg gagtggaccg tccgcgccga caaggccggc   180
accaccccgc tgaccctccg gttcgccaac ggcaccaccg tcaaccgccc gatgaccatc   240
agcgtcaacg gcaccccggc cctcacgggc cgctccttcc ccggcaacgg gtcctggacg   300
agctggcaga cggccaacct cgacgtcccc ctcagagagg cgacaacac gatccgggcc   360
accgcgacca ccgccaacgg cggccccaac gtcgacagcc tcaccgtccc g            411
```

<210> SEQ ID NO 5
<211> LENGTH: 63
<212> TYPE: PRT
<213> ORGANISM: Teredinibacter turnerae
<220> FEATURE:
<223> OTHER INFORMATION: linker

<400> SEQUENCE: 5

```
Gly Gly Gly Ser Gly Ser Ser Thr Ser Ser Thr Ser Ser Ser Ser Ser
1               5                   10                  15

Ser Ser Ser Ser Ser Ser Ser Ser Ser Ser Ser Ser Ser Ser
            20                  25                  30

Gly Val Ala Ser Ser Ser Ser Ser Ser Ser Ser Ser Ser Ser
        35                  40                  45

Ser Ser Ser Ser Ser Ser Ser Ser Ser Ser Gly Ser Gly
        50                  55                  60
```

<210> SEQ ID NO 6
<211> LENGTH: 189
<212> TYPE: DNA
<213> ORGANISM: Teredinibacter turnerae
<220> FEATURE:
<223> OTHER INFORMATION: linker

<400> SEQUENCE: 6

```
ggcggtggta gcggttcatc gacatcgtct accagttctt caagcagctc gtcttccagc    60
agttcgtcca gctcttcgag cagttcatcg agctcgggtg tggcgtcatc cagctcgtct   120
tcgtccagca gcagttcatc gtcgagcagt tcctcctcca gcagcagttc gagctccagt   180
ggctcaggc                                                           189
```

```
<210> SEQ ID NO 7
<211> LENGTH: 17
<212> TYPE: PRT
<213> ORGANISM: Streptomyces clavuligerus
<220> FEATURE:
<223> OTHER INFORMATION: linker

<400> SEQUENCE: 7
```

Asp Ser Gly Gly Pro Gly Pro Gly Pro Gly Pro Gly Pro Gly Gly Thr
1               5                   10                  15

Pro

```
<210> SEQ ID NO 8
<211> LENGTH: 51
<212> TYPE: DNA
<213> ORGANISM: Streptomyces clavuligerus
<220> FEATURE:
<223> OTHER INFORMATION: linker

<400> SEQUENCE: 8
```

```
gactccgggg gacccggccc cggccccgga cccggcccgg cggcacccc c              51
```

```
<210> SEQ ID NO 9
<211> LENGTH: 12
<212> TYPE: PRT
<213> ORGANISM: Artificial Sequence
<220> FEATURE:
<223> OTHER INFORMATION: catalytic domain motif

<400> SEQUENCE: 9
```

Thr Thr Arg Tyr Trp Asp Cys Cys Lys Pro Ser Cys
1               5                   10

```
<210> SEQ ID NO 10
<211> LENGTH: 36
<212> TYPE: DNA
<213> ORGANISM: Artificial Sequence
<220> FEATURE:
<223> OTHER INFORMATION: catalytic domain motif

<400> SEQUENCE: 10
```

```
acgacccggt actgggactg ctgcaagccg agctgc                              36
```

```
<210> SEQ ID NO 11
<211> LENGTH: 232
<212> TYPE: PRT
<213> ORGANISM: Artificial Sequence
<220> FEATURE:
<223> OTHER INFORMATION: cellulase

<400> SEQUENCE: 11
```

Val Pro Asp Ser Gly Gly Pro Gly Pro Gly Pro Gly Pro Gly Pro Gly
1               5                   10                  15

Gly Thr Pro Gly Ser Gly Gln Thr Thr Arg Tyr Trp Asp Cys Cys Lys
            20                  25                  30

Pro Ser Cys Ala Trp Pro Gly Lys Gly Pro Ser Ser Pro Val Gln Ala
        35                  40                  45

```
Cys Asp Lys Asn Asp Asn Pro Leu Asn Asp Gly Gly Ser Thr Arg Ser
         50                  55                  60

Gly Cys Asp Ala Gly Gly Ser Ala Tyr Met Cys Ser Ser Gln Ser Pro
 65                  70                  75                  80

Trp Ala Val Ser Asp Glu Leu Ser Tyr Gly Trp Ala Ala Val Lys Leu
                 85                  90                  95

Ala Gly Ser Ser Glu Ser Gln Trp Cys Cys Ala Cys Tyr Glu Leu Thr
                100                 105                 110

Phe Thr Ser Gly Pro Val Ala Gly Lys Lys Met Ile Val Gln Ala Thr
            115                 120                 125

Asn Thr Gly Gly Asp Leu Gly Asp Asn His Phe Asp Leu Ala Ile Pro
        130                 135                 140

Gly Gly Gly Val Gly Ile Phe Asn Ala Cys Thr Asp Gln Tyr Gly Ala
145                 150                 155                 160

Pro Pro Asn Gly Trp Gly Asp Arg Tyr Gly Gly Ile His Ser Lys Glu
                165                 170                 175

Glu Cys Glu Ser Phe Pro Glu Ala Leu Lys Pro Gly Cys Asn Trp Arg
            180                 185                 190

Phe Asp Trp Phe Gln Asn Ala Asp Asn Pro Ser Val Thr Phe Gln Glu
        195                 200                 205

Val Ala Cys Pro Ser Glu Leu Thr Ser Lys Ser Gly Cys Ser Arg Gly
210                 215                 220

Ser Gly His His His His His His
225                 230

<210> SEQ ID NO 12
<211> LENGTH: 696
<212> TYPE: DNA
<213> ORGANISM: Artificial Sequence
<220> FEATURE:
<223> OTHER INFORMATION: cellulase

<400> SEQUENCE: 12
gttccagact ctggtggtcc aggtccaggt ccaggtccag gtccaggtgg taccccaggt      60
tctggtcaaa ccactagata ctgggactgt tgtaagccat cttgtgcttg gccaggtaag     120
ggtccatctt ccccagttca agcttgtgac aagaacgaca acccattgaa cgacggtggt     180
tctaccagat ccggttgtga cgctggtggt tctgcttaca tgtgttcttc ccaatctcca     240
tgggctgttt ctgacgagtt gtcttacggt tgggctgccg ttaagttggc tggttcttcc     300
gagtctcaat ggtgttgtgc ttgttacgag ttgaccttca cttctggtcc agttgctggt     360
aagaagatga ttgttcaagc taccaacact ggtggtgact gggtgacaa ccacttcgac      420 ttggctattc caggtggtgg agttggtatt ttcaacgctt gtaccgacca atacggtgct     480
ccacctaacg gttggggtga cagatacggt ggtattcact ctaaggagga atgtgagtct     540
ttcccagagg ctttgaagcc aggttgtaac tggagattcg actggttcca aaacgctgac     600
aacccatctg ttaccttcca agaggttgct tgtccatctg agttgacctc taagtccggt     660
tgttctagag gttccggtca tcaccaccat catcac                               696

<210> SEQ ID NO 13
<211> LENGTH: 404
<212> TYPE: PRT
<213> ORGANISM: Artificial Sequence
<220> FEATURE:
<223> OTHER INFORMATION: cellulase
```

<400> SEQUENCE: 13

```
Ala Asp Ala Leu Pro Ala Asp Arg Ala Pro Arg Ala Ala Val Leu Glu
1               5                   10                  15
Ala Glu Asp Ala Thr Ile Ser Gln Gly Ala Val Glu Ser Asn His Arg
            20                  25                  30
Gly Tyr Thr Gly Arg Gly Phe Val Asn Tyr Asp Asn Leu Thr Gly Ser
        35                  40                  45
Ser Val Glu Trp Thr Val Arg Ala Asp Lys Ala Gly Thr Thr Pro Leu
    50                  55                  60
Thr Leu Arg Phe Ala Asn Gly Thr Thr Val Asn Arg Pro Met Thr Ile
65                  70                  75                  80
Ser Val Asn Gly Thr Pro Ala Leu Thr Gly Arg Ser Phe Pro Gly Asn
                85                  90                  95
Gly Ser Trp Thr Ser Trp Gln Thr Ala Asn Leu Asp Val Pro Leu Arg
            100                 105                 110
Glu Gly Asp Asn Thr Ile Arg Ala Thr Ala Thr Thr Ala Asn Gly Gly
        115                 120                 125
Pro Asn Val Asp Ser Leu Thr Val Pro Gly Gly Ser Gly Ser Ser
    130                 135                 140
Thr Ser Ser Thr Ser Ser Ser Ser Ser Ser Ser Ser Ser Ser Ser Ser
145                 150                 155                 160
Ser Ser Ser Ser Ser Ser Ser Ser Gly Val Ala Ser Ser Ser Ser
                165                 170                 175
Ser Ser Ser Ser Ser Ser Ser Ser Ser Ser Ser Ser Ser Ser Ser
                180                 185                 190
Ser Ser Ser Ser Gly Ser Gly Gly Ser Gly Gln Thr Thr Arg Tyr
            195                 200                 205
Trp Asp Cys Cys Lys Pro Ser Cys Ala Trp Pro Gly Lys Gly Pro Ser
    210                 215                 220
Ser Pro Val Gln Ala Cys Asp Lys Asn Asp Asn Pro Leu Asn Asp Gly
225                 230                 235                 240
Gly Ser Thr Arg Ser Gly Cys Asp Ala Gly Gly Ser Ala Tyr Met Cys
            245                 250                 255
Ser Ser Gln Ser Pro Trp Ala Val Ser Asp Glu Leu Ser Tyr Gly Trp
        260                 265                 270
Ala Ala Val Lys Leu Ala Gly Ser Ser Glu Ser Gln Trp Cys Cys Ala
    275                 280                 285
Cys Tyr Glu Leu Thr Phe Thr Ser Gly Pro Val Ala Gly Lys Lys Met
290                 295                 300
Ile Val Gln Ala Thr Asn Thr Gly Gly Asp Leu Gly Asp Asn His Phe
305                 310                 315                 320
Asp Leu Ala Ile Pro Gly Gly Gly Val Gly Ile Phe Asn Ala Cys Thr
                325                 330                 335
Asp Gln Tyr Gly Ala Pro Pro Asn Gly Trp Gly Asp Arg Tyr Gly Gly
            340                 345                 350
Ile His Ser Lys Glu Glu Cys Glu Ser Phe Pro Glu Ala Leu Lys Pro
        355                 360                 365
Gly Cys Asn Trp Arg Phe Asp Trp Phe Gln Asn Ala Asp Asn Pro Ser
    370                 375                 380
Val Thr Phe Gln Glu Val Ala Cys Pro Ser Glu Leu Thr Ser Lys Ser
385                 390                 395                 400
Gly Cys Ser Arg
```

<210> SEQ ID NO 14
<211> LENGTH: 1212
<212> TYPE: DNA
<213> ORGANISM: Artificial Sequence
<220> FEATURE:
<223> OTHER INFORMATION: cellulase

<400> SEQUENCE: 14

| | | | | | |
|---|---|---|---|---|---|
| gcggacgccc | tccccgcgga | ccgcgccccc | cgggccgccg | tgctcgaggc | cgaggacgcg | 60 |
| accatctccc | agggcgcggt | cgagtccaac | caccgcggct | acaccggccg | gggcttcgtc | 120 |
| aactacgaca | acctcaccgg | cagcagtgtg | gagtggaccg | tccgcgccga | caaggccggc | 180 |
| accaccccgc | tgaccctccg | gttcgccaac | ggcaccaccg | tcaaccgccc | gatgaccatc | 240 |
| agcgtcaacg | gcaccccggc | cctcacgggc | cgctccttcc | ccggcaacgg | gtcctggacg | 300 |
| agctggcaga | cggccaacct | cgacgtcccc | ctcagagagg | cgacaacac | gatccgggcc | 360 |
| accgcgacca | ccgccaacgg | cggccccaac | gtcgacagcc | tcaccgtccc | gggcggtggt | 420 |
| agcggttcat | cgacatcgtc | taccagttct | tcaagcagct | cgtcttccag | cagttcgtcc | 480 |
| agctcttcga | gcagttcatc | gagctcgggt | gtggcgtcat | ccagctcgtc | ttcgtccagc | 540 |
| agcagttcat | cgtcgagcag | ttcctcctcc | agcagcagtt | cgagctccag | tggctcaggc | 600 |
| ggcagcggcc | agacgacccg | gtactgggac | tgctgcaagc | cgagctgcgc | ctggcccggc | 660 |
| aagggccccct | cgtctccggt | gcaggcctgc | gacaagaacg | acaacccgct | caacgacggc | 720 |
| ggctccaccc | ggtccggctg | cgacgcgggc | ggcagcgcct | acatgtgctc | ctcccagagc | 780 |
| ccctgggcca | tcagcgacga | gctgtcgtac | ggctgggcgg | ccgtcaagct | cgccggcagc | 840 |
| tccgagtcgc | agtggtgctg | cgcctgctac | gagctgacct | tcaccagcgg | gccggtcgcg | 900 |
| ggcaagaaga | tgattgtgca | ggcgaccaac | accggtggcg | acctgggcga | caaccacttt | 960 |
| gacctggcca | tccccggtgg | cggtgtcggt | attttcaacg | cctgcaccga | ccagtacggc | 1020 |
| gctccccga | acggctgggg | cgaccgctac | ggcggcatcc | attccaagga | agagtgcgaa | 1080 |
| tccttcccgg | aggccctcaa | gcccggctgc | aactggcgct | cgactggtt | ccaaaacgcc | 1140 |
| gacaacccgt | cggtcacctt | ccaggaggtg | gcctgcccgt | cggagctcac | gtccaagagc | 1200 |
| ggctgctccc | gt | | | | | 1212 |

<210> SEQ ID NO 15
<211> LENGTH: 358
<212> TYPE: PRT
<213> ORGANISM: Artificial Sequence
<220> FEATURE:
<223> OTHER INFORMATION: cellulase

<400> SEQUENCE: 15

Ala Asp Ala Leu Pro Ala Asp Arg Ala Pro Arg Ala Ala Val Leu Glu
1               5                   10                  15

Ala Glu Asp Ala Thr Ile Ser Gln Gly Ala Val Glu Ser Asn His Arg
            20                  25                  30

Gly Tyr Thr Gly Arg Gly Phe Val Asn Tyr Asp Asn Leu Thr Gly Ser
        35                  40                  45

Ser Val Glu Trp Thr Val Arg Ala Asp Lys Ala Gly Thr Thr Pro Leu
    50                  55                  60

Thr Leu Arg Phe Ala Asn Gly Thr Thr Val Asn Arg Pro Met Thr Ile
65                  70                  75                  80

Ser Val Asn Gly Thr Pro Ala Leu Thr Gly Arg Ser Phe Pro Gly Asn
                85                  90                  95

Gly Ser Trp Thr Ser Trp Gln Thr Ala Asn Leu Asp Val Pro Leu Arg
            100                 105                 110

Glu Gly Asp Asn Thr Ile Arg Ala Thr Ala Thr Ala Asn Gly Gly
        115                 120                 125

Pro Asn Val Asp Ser Leu Thr Val Pro Asp Ser Gly Pro Gly Pro
    130                 135                 140

Gly Pro Gly Pro Gly Pro Gly Gly Thr Pro Gly Ser Gly Gln Thr Thr
145                 150                 155                 160

Arg Tyr Trp Asp Cys Cys Lys Pro Ser Cys Ala Trp Pro Gly Lys Gly
                165                 170                 175

Pro Ser Ser Pro Val Gln Ala Cys Asp Lys Asn Asp Asn Pro Leu Asn
            180                 185                 190

Asp Gly Gly Ser Thr Arg Ser Gly Cys Asp Ala Gly Gly Ser Ala Tyr
        195                 200                 205

Met Cys Ser Ser Gln Ser Pro Trp Ala Val Ser Asp Glu Leu Ser Tyr
    210                 215                 220

Gly Trp Ala Ala Val Lys Leu Ala Gly Ser Ser Glu Ser Gln Trp Cys
225                 230                 235                 240

Cys Ala Cys Tyr Glu Leu Thr Phe Thr Ser Gly Pro Val Ala Gly Lys
                245                 250                 255

Lys Met Ile Val Gln Ala Thr Asn Thr Gly Gly Asp Leu Gly Asp Asn
            260                 265                 270

His Phe Asp Leu Ala Ile Pro Gly Gly Gly Val Gly Ile Phe Asn Ala
        275                 280                 285

Cys Thr Asp Gln Tyr Gly Ala Pro Pro Asn Gly Trp Gly Asp Arg Tyr
    290                 295                 300

Gly Gly Ile His Ser Lys Glu Glu Cys Glu Ser Phe Pro Glu Ala Leu
305                 310                 315                 320

Lys Pro Gly Cys Asn Trp Arg Phe Asp Trp Phe Gln Asn Ala Asp Asn
                325                 330                 335

Pro Ser Val Thr Phe Gln Glu Val Ala Cys Pro Ser Glu Leu Thr Ser
            340                 345                 350

Lys Ser Gly Cys Ser Arg
        355

<210> SEQ ID NO 16
<211> LENGTH: 1074
<212> TYPE: DNA
<213> ORGANISM: Artificial Sequence
<220> FEATURE:
<223> OTHER INFORMATION: cellulase

<400> SEQUENCE: 16

| | | | | | |
|---|---|---|---|---|---|
| gcggacgccc | tccccgcgga | ccgcgccccc | cgggccgccg | tgctcgaggc | cgaggacgcg | 60 |
| accatctccc | agggcgcggt | cgagtccaac | caccgcggct | acaccggccg | gggcttcgtc | 120 |
| aactacgaca | acctcaccgg | cagcagtgtg | gagtggaccg | tccgcgccga | caaggccggc | 180 |
| accaccccgc | tgaccctccg | gttcgccaac | ggcaccaccg | tcaaccgccc | gatgaccatc | 240 |
| agcgtcaacg | gcacccggc | cctcacgggc | cgctccttcc | ccggcaacgg | gtcctggacg | 300 |
| agctggcaga | cggccaacct | cgacgtcccc | ctcagagagg | gcgacaacac | gatccgggcc | 360 |
| accgcgacca | ccgccaacgg | cggcccaac | gtcgacagcc | tcaccgtccc | ggactccggg | 420 |
| ggacccggcc | ccgccccgg | accggccccg | ggcggcaccc | ccggcagcgg | ccagacgacc | 480 |
| cggtactggg | actgctgcaa | gccgagctgc | gcctggcccg | gcaagggccc | ctcgtctccg | 540 |

```
gtgcaggcct gcgacaagaa cgacaacccg ctcaacgacg gcggctccac ccggtccggc    600
tgcgacgcgg gcggcagcgc ctacatgtgc tcctcccaga gccctgggc cgtcagcgac    660 gagctgtcgt acggctgggc ggccgtcaag ctcgccggca gctccgagtc gcagtggtgc    720
tgcgcctgct acgagctgac cttcaccagc gggccggtcg cgggcaagaa gatgattgtg    780
caggcgacca acaccggtgg cgacctgggc gacaaccact ttgacctggc catccccggt    840
ggcggtgtcg gtattttcaa cgcctgcacc gaccagtacg cgctcccccc gaacggctgg    900
ggcgaccgct acggcggcat ccattccaag gaagagtgcg aatccttccc ggaggccctc    960
aagcccggct gcaactggcg cttcgactgg ttccaaaacg ccgacaaccc gtcggtcacc   1020
ttccaggagg tggcctgccc gtcggagctc acgtccaaga gcggctgctc ccgt         1074
```

<210> SEQ ID NO 17
<211> LENGTH: 365
<212> TYPE: PRT
<213> ORGANISM: Artificial Sequence
<220> FEATURE:
<223> OTHER INFORMATION: cellulase

<400> SEQUENCE: 17

```
Ala Asp Ala Leu Pro Ala Asp Arg Ala Pro Arg Ala Ala Val Leu Glu
1               5                   10                  15

Ala Glu Asp Ala Thr Ile Ser Gln Gly Ala Val Glu Ser Asn His Arg
            20                  25                  30

Gly Tyr Thr Gly Arg Gly Phe Val Asn Tyr Asp Asn Leu Thr Gly Ser
        35                  40                  45

Ser Val Glu Trp Thr Val Arg Ala Asp Lys Ala Gly Thr Thr Pro Leu
    50                  55                  60

Thr Leu Arg Phe Ala Asn Gly Thr Thr Val Asn Arg Pro Met Thr Ile
65                  70                  75                  80

Ser Val Asn Gly Thr Pro Ala Leu Thr Gly Arg Ser Phe Pro Gly Asn
                85                  90                  95

Gly Ser Trp Thr Ser Trp Gln Thr Ala Asn Leu Asp Val Pro Leu Arg
            100                 105                 110

Glu Gly Asp Asn Thr Ile Arg Ala Thr Ala Thr Thr Ala Asn Gly Gly
        115                 120                 125

Pro Asn Val Asp Ser Leu Thr Val Pro Asn Asp Pro Leu Pro Gly
    130                 135                 140

Lys Asn Thr Pro Thr Pro Thr Pro Thr Ser Ala Pro Leu Ser Ser
145                 150                 155                 160

Gly Gly Ser Gly Gln Thr Thr Arg Tyr Trp Asp Cys Cys Lys Pro Ser
                165                 170                 175

Cys Ala Trp Pro Gly Lys Gly Pro Ser Ser Pro Val Gln Ala Cys Asp
            180                 185                 190

Lys Asn Asp Asn Pro Leu Asn Asp Gly Gly Ser Thr Arg Ser Gly Cys
        195                 200                 205

Asp Ala Gly Gly Ser Ala Tyr Met Cys Ser Ser Gln Ser Pro Trp Ala
    210                 215                 220

Val Ser Asp Glu Leu Ser Tyr Gly Trp Ala Ala Val Lys Leu Ala Gly
225                 230                 235                 240

Ser Ser Glu Ser Gln Trp Cys Cys Ala Cys Tyr Glu Leu Thr Phe Thr
                245                 250                 255

Ser Gly Pro Val Ala Gly Lys Lys Met Ile Val Gln Ala Thr Asn Thr
            260                 265                 270
```

Gly Gly Asp Leu Gly Asp Asn His Phe Asp Leu Ala Ile Pro Gly Gly
        275                 280                 285

Gly Val Gly Ile Phe Asn Ala Cys Thr Asp Gln Tyr Gly Ala Pro Pro
    290                 295                 300

Asn Gly Trp Gly Asp Arg Tyr Gly Gly Ile His Ser Lys Glu Glu Cys
305                 310                 315                 320

Glu Ser Phe Pro Glu Ala Leu Lys Pro Gly Cys Asn Trp Arg Phe Asp
                325                 330                 335

Trp Phe Gln Asn Ala Asp Asn Pro Ser Val Thr Phe Gln Glu Val Ala
            340                 345                 350

Cys Pro Ser Glu Leu Thr Ser Lys Ser Gly Cys Ser Arg
        355                 360                 365

<210> SEQ ID NO 18
<211> LENGTH: 1095
<212> TYPE: DNA
<213> ORGANISM: Artificial Sequence
<220> FEATURE:
<223> OTHER INFORMATION: cellulase

<400> SEQUENCE: 18
gcggacgccc tccccgcgga ccgcgccccc cgggccgccg tgctcgaggc cgaggacgcg      60
accatctccc agggcgcggt cgagtccaac caccgcggct acaccggccg ggcttcgtc     120 aactacgaca acctcaccgg cagcagtgtg gagtggaccg tccgcgccga caaggccggc     180
accaccccgc tgaccctccg gttcgccaac ggcaccaccg tcaaccgccc gatgaccatc     240
agcgtcaacg gcaccccggc cctcacgggc cgctccttcc ccggcaacgg gtcctggacg     300
agctggcaga cggccaacct cgacgtcccc ctcagagagg cgacaacac gatccgggcc      360 accgcgacca ccgccaacgg cggccccaac gtcgacagcc tcaccgtccc gaacgacgac     420
ccacttccag gaaagaacac gcctacgcct actccaacga cgtctgcgcc cttgtcttct     480
ggtggcagcg gccagacgac ccggtactgg gactgctgca agccgagctg cgcctggccc     540
ggcaagggcc cctcgtctcc ggtgcaggcc tgcgacaaga cgacaaccc gctcaacgac      600 ggcggctcca cccggtccgg ctgcgacgcg ggcggcagcc cctacatgtg ctcctcccag     660 agccccctggg ccgtcagcga cgagctgtcg tacggctggg cggccgtcaa gctcgccggc     720
agctccgagt cgcagtggtg ctgcgcctgc tacgagctga ccttcaccag cgggccggtc     780
gcgggcaaga agatgattgt gcaggcgacc aacaccggtg gcgacctggg cgacaaccac     840
tttgacctgg ccatccccgg tggcggtgtc ggtattttca acgcctgcac cgaccagtac     900
ggcgctcccc cgaacggctg gggcgaccgc tacggcggca tccattccaa ggaagagtgc     960
gaatccttcc cggaggccct caagcccggc tgcaactggc gcttcgactg gttccaaaac    1020
gccgacaacc cgtcggtcac cttccaggag gtggcctgcc cgtcggagct cacgtccaag    1080
agcggctgct cccgt                                                     1095

<210> SEQ ID NO 19
<211> LENGTH: 15
<212> TYPE: PRT
<213> ORGANISM: Artificial Sequence
<220> FEATURE:
<223> OTHER INFORMATION: carbohydrate binding domain tag

<400> SEQUENCE: 19

Val Pro Asp Ser Gly Gly Pro Gly Pro Gly Pro Gly Pro Gly Pro
1               5                   10                  15

<210> SEQ ID NO 20
<211> LENGTH: 45
<212> TYPE: DNA
<213> ORGANISM: Artificial Sequence
<220> FEATURE:
<223> OTHER INFORMATION: carbohydrate binding domain tag

<400> SEQUENCE: 20
gttccagact ctggtggtcc aggtccaggt ccaggtccag gtcca            45

<210> SEQ ID NO 21
<211> LENGTH: 12
<212> TYPE: PRT
<213> ORGANISM: artificial sequence
<220> FEATURE:
<223> OTHER INFORMATION: sequence motif is not specific for any organism
<220> FEATURE:
<221> NAME/KEY: VARIANT
<222> LOCATION: (1)..(1)
<223> OTHER INFORMATION: Xaa is any amino acid selected from the group
      consisting of serine, threonine and alanine
<220> FEATURE:
<221> NAME/KEY: VARIANT
<222> LOCATION: (5)..(5)
<223> OTHER INFORMATION: Xaa is any amino acid selected from the group
      consisting of phenylalanine, tyrosine and tryptophan
<220> FEATURE:
<221> NAME/KEY: VARIANT
<222> LOCATION: (7)..(11)
<223> OTHER INFORMATION: Xaa is any amino acid
<220> FEATURE:
<221> NAME/KEY: VARIANT
<222> LOCATION: (12)..(12)
<223> OTHER INFORMATION: Xaa is any amino acid selected from the group
      consisting of cysteine and alanine

<400> SEQUENCE: 21

Xaa Thr Arg Tyr Xaa Asp Xaa Xaa Xaa Xaa Xaa Xaa
1               5                   10

<210> SEQ ID NO 22
<211> LENGTH: 15
<212> TYPE: PRT
<213> ORGANISM: artificial sequence
<220> FEATURE:
<223> OTHER INFORMATION: sequence motif is not specific for any organism
<220> FEATURE:
<221> NAME/KEY: VARIANT
<222> LOCATION: (2)..(2)
<223> OTHER INFORMATION: Xaa is any amino acid selected from the group
      consisting of proline, serine and cysteine
<220> FEATURE:
<221> NAME/KEY: VARIANT
<222> LOCATION: (3)..(3)
<223> OTHER INFORMATION: Xaa is any amino acid selected from the group
      consisting of aspartate, glutamine, glutamate and asparagine

<400> SEQUENCE: 22

Val Xaa Xaa Ser Gly Gly Pro Gly Pro Gly Pro Gly Pro Gly Pro
1               5                   10                  15

<210> SEQ ID NO 23
<211> LENGTH: 12
<212> TYPE: PRT
<213> ORGANISM: artificial sequence
<220> FEATURE:
<223> OTHER INFORMATION: sequence motif is not specific for any organism
<220> FEATURE:
<221> NAME/KEY: VARIANT
<222> LOCATION: (5)..(5)
<223> OTHER INFORMATION: Xaa is any amino acid selected from the group

```
              consisting of phenylalanine, tyrosine and tryptophan
<220> FEATURE:
<221> NAME/KEY: VARIANT
<222> LOCATION: (7)..(11)
<223> OTHER INFORMATION: Xaa is any amino acid
<220> FEATURE:
<221> NAME/KEY: VARIANT
<222> LOCATION: (12)..(12)
<223> OTHER INFORMATION: Xaa is any amino acid selected from the group
              consisting of cysteine and alanine

<400> SEQUENCE: 23

Thr Thr Arg Tyr Xaa Asp Xaa Xaa Xaa Xaa Xaa Xaa
1               5                   10

<210> SEQ ID NO 24
<211> LENGTH: 12
<212> TYPE: PRT
<213> ORGANISM: artificial sequence
<220> FEATURE:
<223> OTHER INFORMATION: sequence motif is not specific to any organism
<220> FEATURE:
<221> NAME/KEY: VARIANT
<222> LOCATION: (7)..(11)
<223> OTHER INFORMATION: Xaa is any amino acid

<400> SEQUENCE: 24

Thr Thr Arg Tyr Trp Asp Xaa Xaa Xaa Xaa Xaa Cys
1               5                   10
```

DETERGENT COMPOSITIONS

The invention relates to a detergent composition comprising a shading dye and a novel cellulase. The invention further relates to methods of doing laundry using such compositions.

Cellulases are used for various applications and are of particular importance for the good performance of cleaning applications such as the performance of detergent compositions.

There are various cellulases known within the art, however, functional requirements are constantly increasing as customers expect high cleaning performance while production costs and thus costs of the final product should be kept low. In addition, environmental aspects gain importance and requirements for marketing approval constantly increase. So far, whiteness of fabrics is often achieved by implementation of bleaching agents such as chlorine-containing compositions. This leads not only to damages of the fabrics but is also increasing costs and environmentally harmful. Such state of the art enzymes are for example disclosed within US 2005 070003 A1.

Owing to the wide array of cellulases and their assorted benefits, laundry compositions frequently contain cellulase blends (i.e. a cellulase for whiteness and a further cellulase for de-pilling, also termed "fabric care").

This increases the enzyme content of the detergent, increasing the cost per dose and the amount of enzyme rinsed away at the end of a wash cycle. Furthermore, the different cellulases may have different stability and activity requirements and optima, making formulation and wash instruction considerations more difficult.

The invention seeks to address these problems through the provision of detergent compositions comprising a cellulase as described herein. Such cellulases may exhibit advantageous dual benefits of both improved laundry whiteness and fabric care (de-fuzzing and de-pilling). This provides both care and cleaning (whiteness) benefits using only one cellulase, rather than two.

The inventors have further observed that synergy is seen between the novel cellulase and a shading dye in the detergent composition.

Accordingly, in a first aspect the present invention provides a detergent composition comprising: —

(a) from 0.0001 to 1 wt. %, preferably from 0.0001 to 0.1 wt. %, more preferably from 0.0001 to 0.01 wt. %, most preferably from 0.0005 to 0.001 wt. % of a shading dye; and, (b) from 0.0001 to 10 wt. %, preferably from 0.0005 to 8 wt. %, more preferably from 0.001 to 5 wt. %, most preferably from 0.002 to 0.2 wt. % of a cellulase selected from any sequence with a sequence identity of at least 80%, preferably at least 85%, further preferred at least 90%, even more preferred at least 92%, also preferred at least 95%, particularly preferred at least 98% and most preferred at least 99% to SEQ ID NO: 11, SEQ ID NO: 13, SEQ ID NO: 15 or SEQ ID NO: 17.

In a second aspect, the invention provides a method of laundering white fabric, the method comprising contacting the fabric with an aqueous solution comprising a composition according to the first aspect, optionally wherein the step of contacting the fabric with the aqueous solution occurs at 30° C. or less.

DETAILED DESCRIPTION OF THE INVENTION

Cellulase

Within the present invention, the term "cellulase" is to be understood as referring to any enzyme catalyzing cellulolysis, which is the decomposition of cellulose and related polysaccharides. Within the present invention, the term "cellulase" also refers to any naturally occurring mixture or complex of such enzymes, which act serially or synergistically to decompose cellulosic material. The cellulase of the present invention may be of fungal, bacterial or protozoal origin. The term "cellulases" refers in particular to any enzyme capable of breaking down cellulose into monosaccharides such as beta-glucose, or shorter polysaccharides and oligosaccharides.

The term "de-pilling" refers to the ability of cellulase enzymes to remove cotton fuzz and loose surface fibers in or on the fabric. This process is also referred to as "depilling", "biopolishing" and "biofinishing" and smoothes the surface of the fabric, which in turn improves its softness and appearance. Cellulase treatment also aids in the prevention of subsequent formation of fiber pills that make the garments appear worn. During de-pilling it is desirable to minimize strength loss of the fabric due to the hydrolytic action of the cellulases.

The inventive cellulase comprises the catalytic domain motive [STA]-T-R-Y-[FYW]-D-x(5)-[CA] (SEQ ID NO: 21). Any motive or modification as referred to within the present application is defined using the one letter code for amino acids well known to a person skilled in the art.

The amino acids are encoded as follows:

G Glycine, P Proline, A Alanine, V Valine, L Leucine, I Isoleucine, M Methionine, C Cysteine, F Phenylalanine, Y Tyrosine, W Tryptophan, H Histidine, K Lysine, R Arginine, Q Glutamine, N Asparagine, E Glutamic Acid, D Aspartic Acid, S Serine, T Threonine.

The amino acids in square brackets are to be understood as alternatives of the respective position. The "x" indicates that the respective position may be selected from all existing amino acids. The number in parenthesis (within this definition referred to as variable "z") (e.g. 5 as contained within the catalytic domain motif) indicates that the term ("term" meaning amino acid or any motive such as [ACT]) in front of the parenthesis is repeated z times (e.g. A(5) indicates that the amino acid A is repeated 5 times). In case there are two numbers indicated e.g. (5, 10), the term (as defined above) in front of the parenthesis may be repeated from 5 to 10 times.

The cellulase may comprise the catalytic domain motif [STA]-T-R-Y-[FYW]-D-x(5)-[CA] (SEQ ID NO: 21) and a carbohydrate binding domain with a sequence identity of at least 80% to SEQ ID NO: 3, or a carbohydrate binding domain comprising the tag motif V-[PSC]-[DQEN]-S-G-G-P-G-P-G-P-G-P-G-P (SEQ ID NO: 22).

Within a preferred embodiment of the present invention, the catalytic domain motif is T-T-R-Y-[FYW]-D-x(5)-[CA] (SEQ ID NO: 23).

Within a particularly preferred embodiment of the present invention, the catalytic domain motif is T-T-R-Y-W-D-x(5)-C (SEQ ID NO: 24) wherein the catalytic domain motive T-T-R-Y-W-D-C-C-K-P-S-C (SEQ ID NO: 9) is most preferred.

The cellulase of the present invention further comprises a carbohydrate binding domain with a sequence identity of at least 80%, preferably at least 85%, further preferred at least 90%, even more preferred at least 92%, also preferred at least 95%, particularly preferred at least 98% and most preferred at least 99% to SEQ ID NO: 3 or a carbohydrate binding tag motif V-[PSC]-[DQEN]-S-G-G-P-G-P-G-P-G-P-G-P (SEQ ID NO: 22), wherein a carbohydrate binding domain tag of V-P-D-S-G-G-P-G-P-G-P-G-P-G-P (SEQ ID NO: 19) is most preferred.

Within the present invention, the term "carbohydrate binding domain tag" refers to any sequence comprising the motif V-[PSC]-[DQEN]-S-G-G-P-G-P-G-P-G-P-G-P (SEQ ID NO: 22) which might be directly connected to the cellulase catalytic domain or via a linker, preferably a linker as defined herein.

The sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows: (Identical Residues×100)/(Length of Alignment−Total Number of Gaps in Alignment)

Within a particularly preferred embodiment, the inventive cellulase comprises a sequence with at least 80%, preferably at least 85%, further preferred at least 90%, even more preferred at least 92%, also preferred at least 95%, particularly preferred at least 98% and most preferred at least 99% sequence identity to SEQ ID NO: 1.

Within a preferred embodiment, the inventive cellulase further comprises a linker. The term "linker" refers to any sequence known to a person skilled in the art as suitable to connect or "link" the catalytic domain and the carbohydrate binding domain or the carbohydrate binding domain tag. "Linkers" or "spacers" are short amino acid sequences created in nature to separate multiple domains in a single protein. The function is to prohibit unwanted interactions between the catalytic domain and the carbohydrate binding domain or the carbohydrate binding domain tag without interfering with the function of each domain. Some linkers have been surprisingly found to contribute to the performance of the novel cellulase and to increase ARD (Anti Re-Deposition) and de-pilling effects and the inventors of the present invention have even been able to identify a linker motif.

Within a preferred embodiment, the linker has a sequence identity of at least 80%, preferably at least 85%, further preferred at least 90%, even more preferred at least 92%, also preferred at least 95%, particularly preferred at least 98% and most preferred at least 99% to SEQ ID NO: 5. It is thereby further preferred that the linker is comprised of amino acids of A, G, S, V, and/or T (5,65).

Within another preferred embodiment, the linker has a sequence identity of at least 80%, preferably at least 85%, further preferred at least 90%, even more preferred at least 92%, also preferred at least 95%, particularly preferred at least 98% and most preferred at least 99% to SEQ ID NO: 7. It is thereby further preferred that the linker comprises an amino acid sequence of ([SG]-P)(5,10).

The cellulase is selected from any sequence with a sequence identity of at least 80%, preferably at least 85%, further preferred at least 90%, even more preferred at least 92%, also preferred at least 95%, particularly preferred at least 98% and most preferred at least 99% to SEQ ID NO: 11, SEQ ID NO: 13, SEQ ID NO: 15 or SEQ ID NO: 17.

The most preferred cellulase is selected from any sequence with a sequence identity of at least 80%, preferably at least 85%, further preferred at least 90%, even more preferred at least 92%, also preferred at least 95%, particularly preferred at least 98% and most preferred at least 99% to SEQ ID NO: 11.

The inventive cellulase may be prepared by any method known to a person skilled in the art as suitable for the inventive purpose. Preferred is the expression of the inventive cellulase by a suitable host cell. The term "host cell" refers to any cell type that is suitable to transformation, transfection, transduction, or the like with a nucleic acid construct or expression vector comprising the nucleic acid sequence of the inventive cellulase. The term "host cell" also encompasses any progeny of a parent cell, which is not identical to the parent cell due to mutations that occur during replication. Host cells are preferably selected from the group consisting of fungi, yeast and bacteria. Within the present invention, the host cell is preferably a yeast cell such as *Candida, Hansenula, Kluyveromyces; Pichia, Saccharomyces, Schizosaccharomyces*, or *Yarrowia* wherein *Kluyveromyces lactis, Kaccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Yarrowia lipolytica* and *Pichia pastoris* are preferred.

The term "expression" includes any step involved in the production of the inventive cellulase such as but not limited to transcription, posttranscriptional, modification, translation, post-translational modification and secretion.

Preferably, the detergent composition comprises from 0.0005 to 8 wt. %, more preferably from 0.001 to 5 wt. %, most preferably from 0.002 to 0.2 wt. % of the cellulase.

Shading Dye

Preferably, the shading dye is a blue or violet shading dye, although other hues are also within the scope of the invention. The use of a blue or violet shading dye may enhance the perception of whiteness and/or cleanness.

Suitable shading dyes are described in WO 2011/047987, the contents of which are incorporated herein by reference in their entirety.

Preferably, the shading dye is a reactive dye covalently bound to a polymer. More preferably, the polymer is a polyimine, optionally but preferably wherein the polyimine is substituted with 2-hydroxypropan-1-yl groups.

The shading dye may preferably comprise a chromophore of formula:

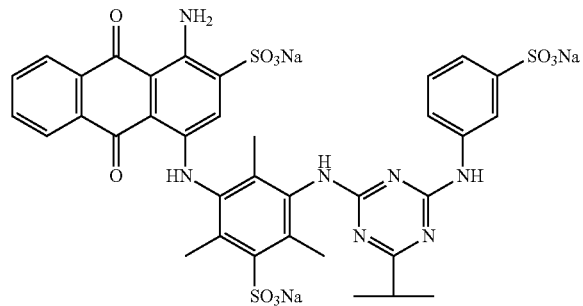

wherein ---- represents a point of attachment.

An exemplary and preferred shading dye is UB40, which has the following structure:

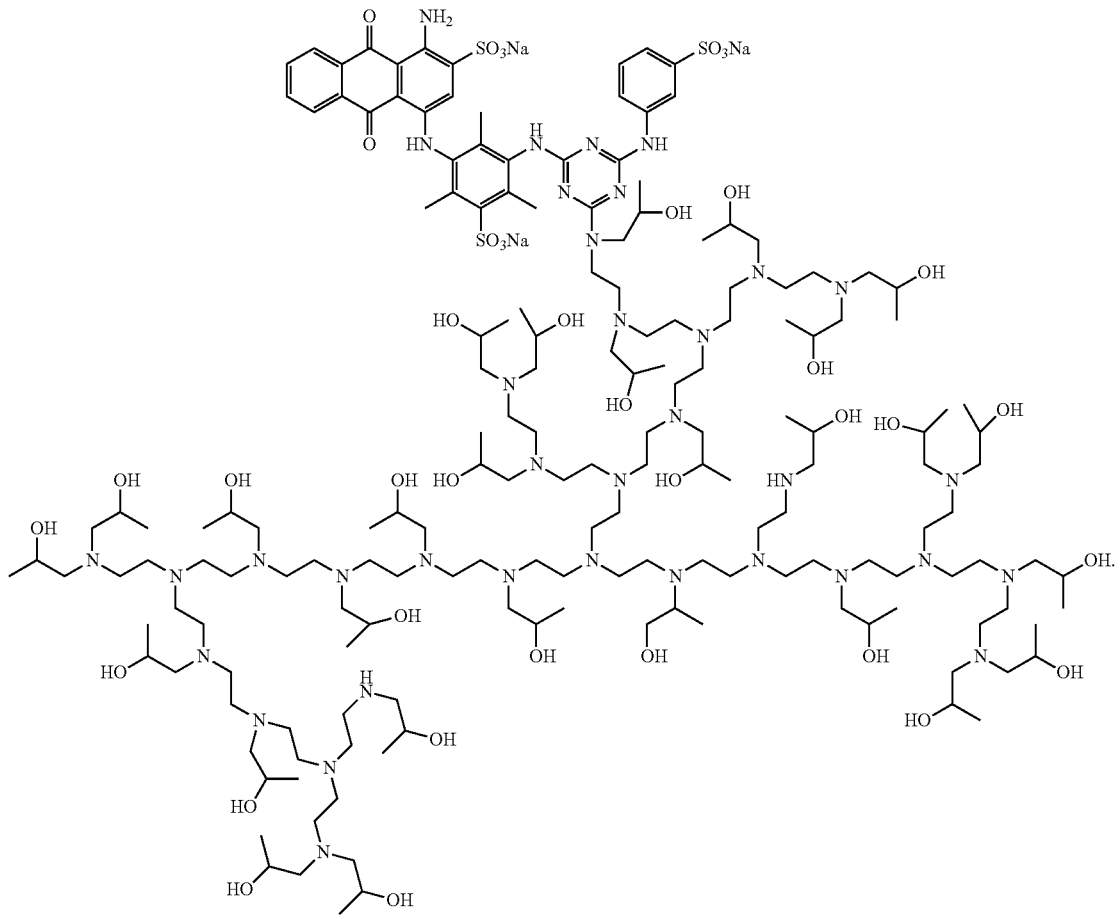

In some cases, the shading dye is preferably a direct dye, for example, an azine dye. Suitable azine dyes are described in WO 2008/017570, the contents of which are incorporated herein by reference in their entirety.

In some cases, the dye is preferably AV50, which has the following structure:

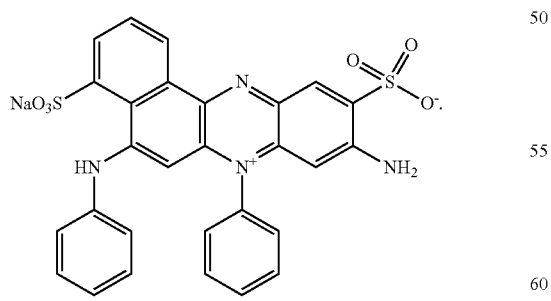

The shading dye is preferably present in the composition in range from 0.0001 to 1 wt %, more preferably from 0.0001 to 0.1 wt. %, even more preferably from 0.0001 to 0.01 wt. %, most preferably from 0.0005 to 0.001 wt %.

Compositions

The detergent composition of the invention may be in any convenient form, such as a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is known to a person skilled in the art as suitable for the inventive purpose and which prevents the release of the composition from the pouch prior to water contact. The pouch is preferably made from water soluble film which encloses an inner volume. The inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, polymethacrylates, most preferably polyvinyl alcohol copolymers and, hydroxypropyl methyl cellulose (HPMC).

A liquid or gel detergent may be aqueous, preferably containing at least 20% by weight and up to 95 weight-% water, such as up to about 70 weight-% water, up to about 65 weight-% water, up to about 55 weight-% water, up to about 45 weight-% water, up to about 35 weight-% water, wherein a water content of from 2 to 40 weight-% is preferred.

Other types of liquids include alkanols, amines, diols, ethers and polyols in an aqueous liquid or gel. An aqueous liquid or gel detergent may contain from 0 to 30 weight-% of an organic solvent. A liquid or gel detergent may also be non-aqueous.

Preferably the detergent composition is a liquid, powder or gel. It may be provided in a capsule or tablet, or in free-pouring form. The detergent compositions may be prepared using any suitable methods known in the art.

Preferably, the composition is a liquid. Liquid compositions are preferred by many consumers, and concentrated liquid products improve sustainability owing to decreased packaging and a smaller transportation footprint. Preferred liquid compositions comprise from 2 to 60 wt. % of surfactant, preferably anionic surfactant and from 5 to 80 wt. % of water.

Surfactant

The composition is a detergent composition and suitably comprises a surfactant. Suitable surfactant levels can be from 0.1 to 80 wt. %, preferably 1 to 70 wt. %, more preferably 2 to 60 wt. %

The detergent composition preferably comprises from 4 to 40 wt. %, more preferably from 5 to 35 wt. %, most preferably from 6 to 33 wt. % of a surfactant.

Suitable surfactants may be chosen from the surfactants described "Surface Active Agents" Vol. 1, by Schwartz & Perry, Interscience 1949, Vol. 2 by Schwartz, Perry & Berch, Interscience 1958, in the current edition of "McCutcheon's Emulsifiers and Detergents" published by Manufacturing Confectioners Company or in "Tenside-Taschenbuch", H. Stache, 2nd Edn., Carl Hauser Verlag, 1981 or in Anionic Surfactants: Organic Chemistry edited by Helmut W. Stache (Marcel Dekker 1996).

It is preferred that an anionic surfactant is present.

Suitable anionic detergent compounds which may be used are usually water-soluble alkali metal salts of organic sulphates and sulphonates having alkyl radicals containing from about 8 to about 22 carbon atoms, the term alkyl being used to include the alkyl portion of higher alkyl radicals.

Examples of suitable synthetic anionic detergent compounds are sodium and potassium alkyl sulphates, especially those obtained by sulphating higher $C_8$ to $C_{18}$ alcohols, produced for example from tallow or coconut oil, Alkyl ether carboxylic acids; sodium and potassium alkyl $C_9$ to $C_{20}$ benzene sulphonates, particularly sodium linear secondary alkyl $C_{10}$ to $C_{15}$ benzene sulphonates; and sodium alkyl glyceryl ether sulphates, especially those ethers of the higher alcohols derived from tallow or coconut oil and synthetic alcohols derived from petroleum.

The anionic surfactant is preferably selected from: linear alkyl benzene sulphonate; alkyl sulphates; alkyl ether sulphates; alkyl ether carboxylates; soaps; alkyl (preferably methyl) ester sulphonates, and mixtures thereof.

Preferred anionic surfactants are selected from: linear alkyl benzene sulphonate; alkyl sulphates; alkyl ether sulphates and mixtures thereof. Preferably the alkyl ether sulphate is a $C_{12}$-$C_{14}$ n-alkyl ether sulphate with an average of 1 to 3EO (ethoxylate) units. Sodium lauryl ether sulphate is particularly preferred (SLES). Preferably the linear alkyl benzene sulphonate is a sodium $C_{11}$ to $C_{15}$ alkyl benzene sulphonates. Preferably the alkyl sulphates is a linear or branched sodium $C_{12}$ to $C_{18}$ alkyl sulphates. Sodium dodecyl sulphate is particularly preferred, (SDS, also known as primary alkyl sulphate).

Preferably two or more anionic surfactant are present, for example linear alkyl benzene sulphonate together with an alkyl ether sulphate.

Most preferably the anionic surfactant is selected from: linear alkyl benzene sulphonates; alkyl sulphates; alkyl ether sulphates; and mixtures thereof.

The composition may comprise anionic and/or non-ionic surfactants.

Suitable nonionic detergent compounds which may be used include, in particular, the reaction products of compounds having an aliphatic hydrophobic group and a reactive hydrogen atom, for example, aliphatic alcohols, acids or amides, especially ethylene oxide either alone or with propylene oxide. Specific nonionic detergent compounds are the condensation products of aliphatic $C_8$ to $C_{18}$ primary or secondary linear or branched alcohols with ethylene oxide.

Preferably the alkyl ethoxylated non-ionic surfactant is a $C_8$ to $C_{18}$ primary alcohol with an average ethoxylation of 7EO to 9EO units.

If a non-ionic surfactant is present, then most preferably the non-ionic surfactant is an alcohol ethoxylate, more preferably a $C_{10}$-$C_{18}$ alcohol ethoxylate having an average of 3-10 moles of ethylene oxide, most preferably a $C_{12}$-$C_{15}$ alcohol ethoxylate having an average of 5-9 moles of ethylene oxide.

A highly preferred surfactant comprises from 4 to 40 wt. %, more preferably from 5 to 35 wt. %, most preferably from 6 to 33 wt. % of a surfactant that comprises an anionic surfactant, preferably comprising linear alkyl benzene sulphonates and nonionic surfactant.

In this preferable surfactant mixture, most preferably the weight fraction of nonionic surfactant to anionic surfactant is <0.5, for example from 0.1 to <0.5. This means that it is preferable that the level of anionic surfactant is greater than the level of nonionic surfactant in the detergent composition.

Further preferred ingredients that can suitably be included in the compositions of the invention include perfume, fluorescent agent, further enzymes, builders, and polymers.

Perfume

Preferably the composition comprises one or more perfumes.

The composition preferably comprises a perfume. The perfume is preferably present in the range from 0.001 to 3 wt. %, more preferably 0.05 to 0.5 wt. %, most preferably 0.1 to 1 wt. %. Many suitable examples of perfumes are provided in the CTFA (Cosmetic, Toiletry and Fragrance Association) 1992 International Buyers Guide, published by CTFA Publications and OPD 1993 Chemicals Buyers Directory 80th Annual Edition, published by Schnell Publishing Co.

Preferably the perfume comprises at least one note (compound) from: alpha-isomethyl ionone, benzyl salicylate; citronellol; coumarin; hexyl cinnamal; linalool; Pentanoic acid, 2-methyl-, ethyl ester; octanal; benzyl acetate; 1,6-octadien-3-ol, 3,7-dimethyl-, 3-acetate; cyclohexanol, 2-(1,1-dimethylethyl)-, 1-acetate; delta-damascone; beta-ionone; verdyl acetate; dodecanal; hexyl cinnamic aldehyde; cyclopentadecanolide; benzeneacetic acid, 2-phenylethyl ester; amyl salicylate; beta-caryophyllene; ethyl undecylenate; geranyl anthranilate; alpha-irone; beta-phenyl ethyl benzoate; alpa-santalol; cedrol; cedryl acetate; cedry formate; cyclohexyl salicyate; gamma-dodecalactone; and, beta phenylethyl phenyl acetate.

Useful components of the perfume include materials of both natural and synthetic origin. They include single compounds and mixtures. Specific examples of such components may be found in the current literature, e.g., in Fenaroli's Handbook of Flavor Ingredients, 1975, CRC Press; Synthetic Food Adjuncts, 1947 by M. B. Jacobs, edited by Van Nostrand; or Perfume and Flavor Chemicals by S. Arctander 1969, Montclair, N.J. (USA).

It is commonplace for a plurality of perfume components to be present in a formulation. In the compositions of the present invention it is envisaged that there will be four or more, preferably five or more, more preferably six or more or even seven or more different perfume components.

In perfume mixtures preferably 15 to 25 wt. % are top notes. Top notes are defined by Poucher (Journal of the Society of Cosmetic Chemists 6(2):80 [1955]). Preferred top-notes are selected from citrus oils, linalool, linalyl acetate, lavender, dihydromyrcenol, rose oxide and cis-3-hexanol.

The International Fragrance Association has published a list of fragrance ingredients (perfums) in 2011, (www.ifraorg.org/en-us/ingredients#.U7Z4hPldWzk).

The Research Institute for Fragrance Materials provides a database of perfumes (fragrances) with safety information.

Some or all of the perfume may be encapsulated, typical perfume components which it is advantageous to encapsulate, include those with a relatively low boiling point, preferably those with a boiling point of less than 300, preferably 100-250 Celsius. It is also advantageous to encapsulate perfume components which have a low C Log P (i.e., those which will have a greater tendency to be partitioned into water), preferably with a C Log P of less than 3.0. These materials, of relatively low boiling point and relatively low C Log P have been called the "delayed blooming" perfume ingredients and include one or more of the following materials:

allyl caproate, amyl acetate, amyl propionate, anisic aldehyde, anisole, benzaldehyde, benzyl acetate, benzyl acetone, benzyl alcohol, benzyl formate, benzyl iso valerate, benzyl propionate, beta gamma hexenol, camphor gum, laevo-carvone, d-carvone, cinnamic alcohol, cinamyl formate, cis-jasmone, cis-3-hexenyl acetate, cuminic alcohol, cyclal c, dimethyl benzyl carbinol, dimethyl benzyl carbinol acetate, ethyl acetate, ethyl aceto acetate, ethyl amyl ketone, ethyl benzoate, ethyl butyrate, ethyl hexyl ketone, ethyl phenyl acetate, eucalyptol, eugenol, fenchyl acetate, flor acetate (tricyclo decenyl acetate), frutene (tricycico decenyl propionate), geraniol, hexenol, hexenyl acetate, hexyl acetate, hexyl formate, hydratropic alcohol, hydroxycitronellal, indone, isoamyl alcohol, iso menthone, isopulegyl acetate, isoquinolone, ligustral, linalool, linalool oxide, linalyl formate, menthone, menthyl acetphenone, methyl amyl ketone, methyl anthranilate, methyl benzoate, methyl benyl acetate, methyl eugenol, methyl heptenone, methyl heptine carbonate, methyl heptyl ketone, methyl hexyl ketone, methyl phenyl carbinyl acetate, methyl salicylate, methyl-n-methyl anthranilate, nerol, octalactone, octyl alcohol, p-cresol, p-cresol methyl ether, p-methoxy acetophenone, p-methyl acetophenone, phenoxy ethanol, phenyl acetaldehyde, phenyl ethyl acetate, phenyl ethyl alcohol, phenyl ethyl dimethyl carbinol, prenyl acetate, propyl bornate, pulegone, rose oxide, safrole, 4-terpinenol, alpha-terpinenol, and/or viridine. It is commonplace for a plurality of perfume components to be present in a formulation. It is envisaged that there will be four or more, preferably five or more, more preferably six or more or even seven or more different perfume components from the list given of delayed blooming perfumes given above present in the perfume.

Another group of perfumes with which the present invention can be applied are the so-called 'aromatherapy' materials. These include many components also used in perfumery, including components of essential oils such as Clary Sage, *Eucalyptus*, Geranium, Lavender, Mace Extract, Neroli, Nutmeg, Spearmint, Sweet Violet Leaf and Valerian.

Fluorescent Agent

Preferably the composition comprises one or more fluorescent agents.

The composition preferably comprises a fluorescent agent (optical brightener). Fluorescent agents are well known and many such fluorescent agents are available commercially. Usually, these fluorescent agents are supplied and used in the form of their alkali metal salts, for example, the sodium salts.

Preferred classes of fluorescer are: Di-styryl biphenyl compounds, e.g. Tinopal® CBS-X, Di-amine stilbene di-sulphonic acid compounds, e.g. Tinopal® DMS pure Xtra and Blankophor® HRH, and Pyrazoline compounds, e.g. Blankophor® SN.

Preferred fluorescers are: sodium 2 (4-styryl-3-sulphophenyl)-2H-napthol[1,2-d]triazole, disodium 4,4'-bis{[(4-anilino-6-(N methyl-N-2 hydroxyethyl) amino 1,3,5-triazin-2-yl)]amino}stilbene-2-2' disulophonate, disodium 4,4'-bis{[(4-anilino-6-morpholino-1,3,5-triazin-2-yl)]amino} stilbene-2-2' disulphonate, and disodium 4,4'-bis(2-sulphostyryl)biphenyl.

The total amount of the fluorescent agent or agents used in the composition is preferably from 0.0001 to 0.5 wt. %, more preferably 0.005 to 2 wt. %, most preferably 0.05 to 0.25 wt. %.

Further Enzymes

Other than the indicated cellulase, further enzymes may preferably be present in the composition.

If present, then the level of each enzyme in the laundry composition of the invention is from 0.0001 wt. % to 0.1 wt. %.

Contemplated further enzymes include proteases, alpha-amylases, other cellulases (cellulases other than those specified in the invention as defined by the claims upon filing), lipases, peroxidases/oxidases, pectate lyases, and mannanases, or mixtures thereof.

Preferably the enzyme is selected from: proteases, alpha-amylases; and lipases.

Builders or Complexing Agents

Builder materials may be present. If present then they are generally selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate and organic sequestrants, such as ethylene diamine tetra-acetic acid.

Examples of precipitating builder materials include sodium orthophosphate and sodium carbonate.

Examples of calcium ion-exchange builder materials include the various types of water-insoluble crystalline or amorphous aluminosilicates, of which zeolites are well known representatives, e.g. zeolite A, zeolite B (also known as zeolite P), zeolite C, zeolite X, zeolite Y and also the zeolite P-type as described in EP-A-0,384,070.

The composition may also contain 0-65% of a builder or complexing agent such as ethylenediaminetetraacetic acid, diethylenetriamine-pentaacetic acid, alkyl- or alkenylsuccinic acid, nitrilotriacetic acid or the other builders mentioned below.

Preferably the laundry cleaning formulation is a non-phosphate built laundry detergent formulation, i.e., contains less than 1 wt. % of phosphate.

Polymers

The composition may preferably comprise one or more polymers. Example polymers are polyethyleneimine, poly (vinylpyrrolidone), poly(vinylpyridine-N-oxide), poly(vinylimidazole), carboxymethylcellulose, poly(ethylene glycol), poly(vinyl alcohol), polycarboxylates such as polyacrylates, maleic/acrylic acid copolymers and lauryl methacrylate/acrylic acid copolymers. A preferred polymer is polyethyleneimine.

Methods and Uses

The invention further relates to methods of laundering fabric. Suitably, at least some of the fabric is white, although it will be appreciated that the compositions described herein may be used on coloured fabric. The term white fabric includes white portions of fabric in a garment, which may be patterned and have two or more coloured sections.

As described herein, the cellulases in the compositions of the invention may be stable at higher temperatures, but show good activity at lower temperatures. Lower temperature washes may be preferable as they are more environmentally friendly, less expensive and, typically, less likely to damage fabrics and trims. The step of contacting the fabric with an aqueous solution comprising a composition of the invention, or the wash step, may occur at 60° C. or less, for example at 50° C. or less, for example at 40° C. or less, for example at 30° C. or less.

EXAMPLES

The invention will now be described with reference to the following non-limiting examples and with reference to the following figures: —

Figure 3:
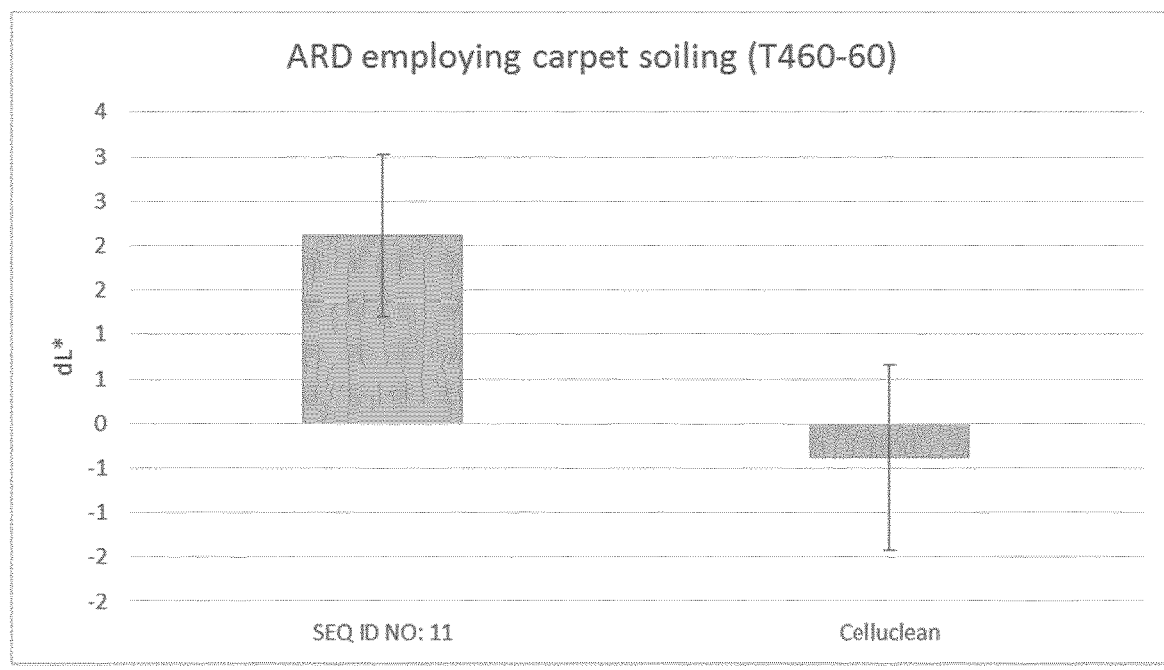
Figure 4:
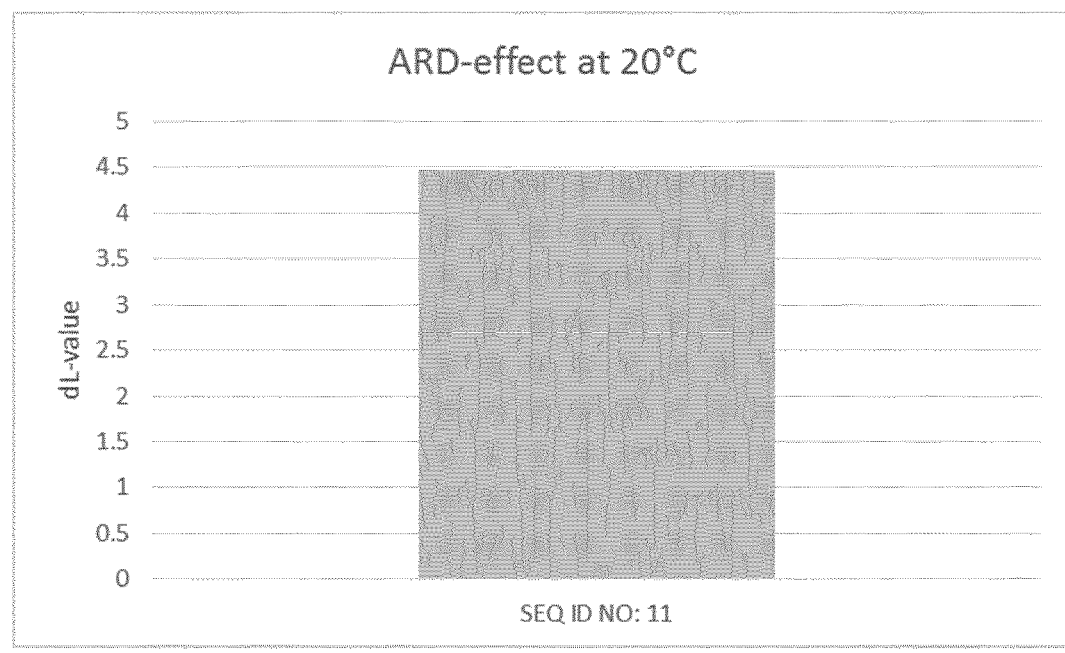
Figure 5:
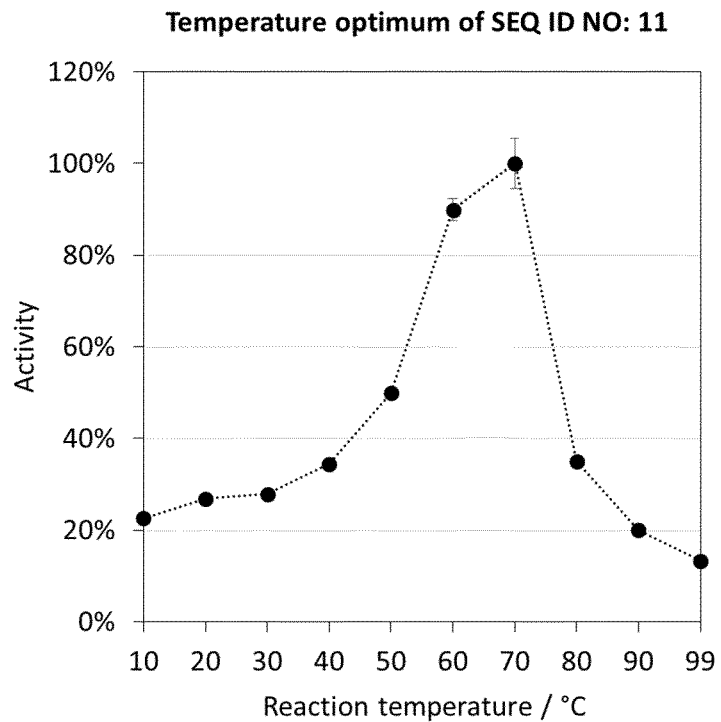
Figure 6:
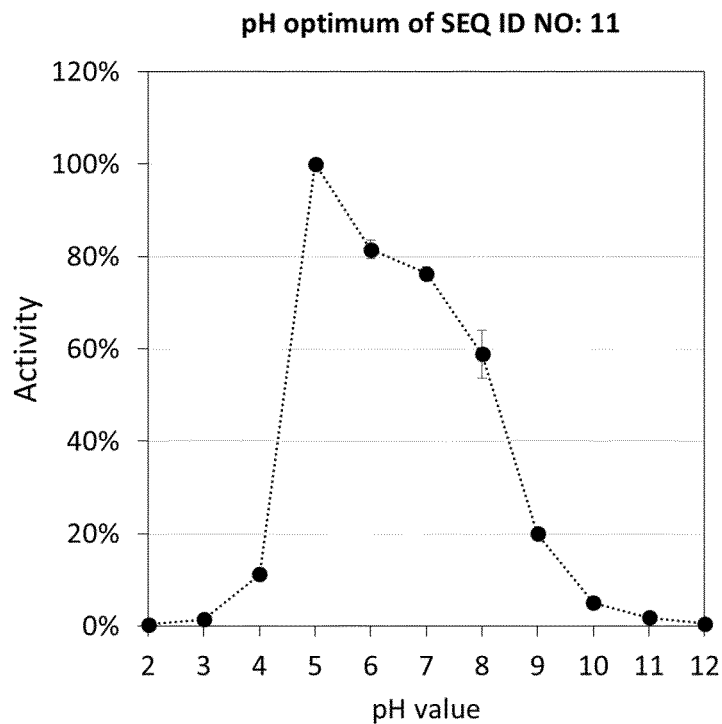
Figure 7:
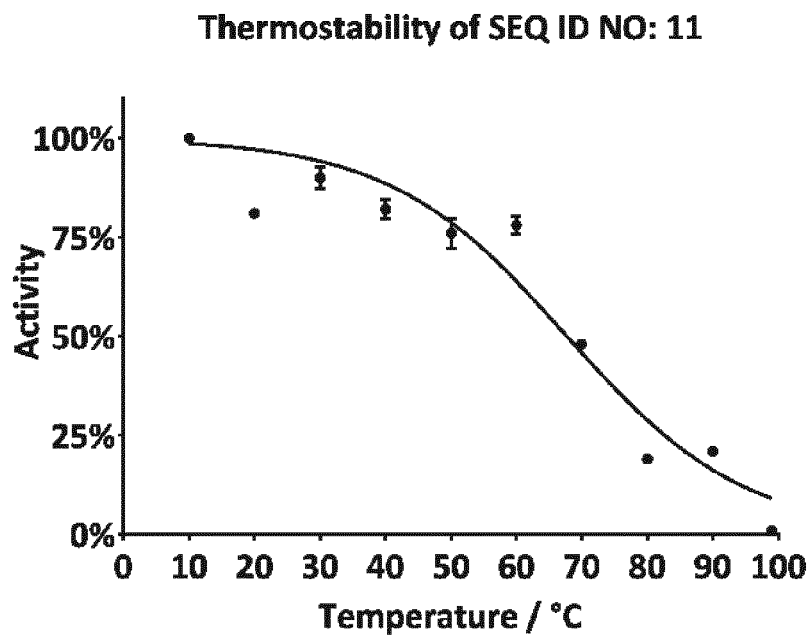

FIG. 3 shows the results of example 6: ARD wash activity of SEQ ID NO: 11 compared to Celluclean® for carpet soil FIG. 4 shows the results of example 8: Applying SEQ ID NO: 11 with a concentration of 0.625 mg/L at 20° C. resulted in a dL* value of 4.5 FIG. 5 shows the results of example 9: The temperature optimum of SEQ ID NO: 11 FIG. 6 shows the results of example 10: The pH optimum of SEQ ID NO: 11 FIG. 7 shows the results of example 11: The thermostability of SEQ ID NO: 11

Figure 8:
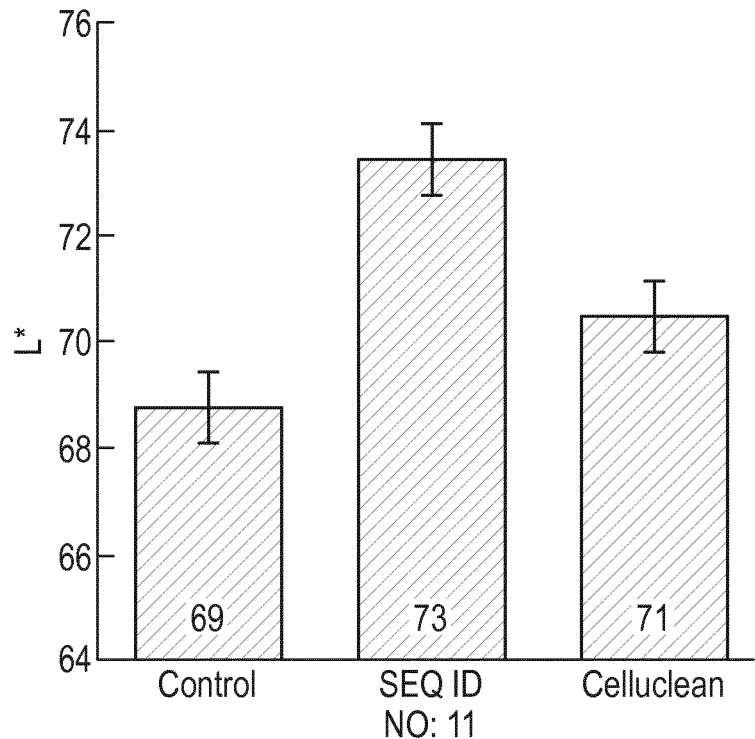

FIG. 8 shows a comparison of whiteness for a cellulase within the definitions for the invention (Cellulase SEQ ID NO: 11) with Celluclean® and a control after 3 washes at 45° C.

Figure 9:
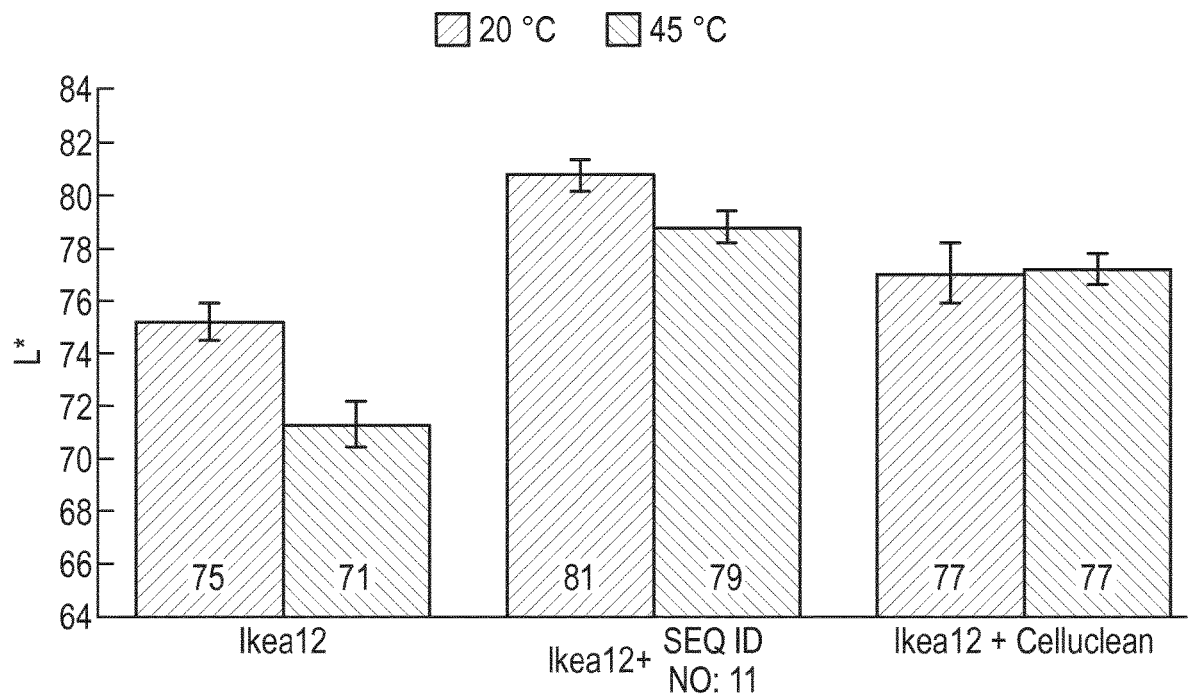

FIG. 9 shows improved whiteness performance for Cellulase SEQ ID NO: 11 compared to Celluclean® in a liquid formulation at different temperatures.

FIG. 10 compares the performance of a composition of the invention (Cellulase SEQ ID NO: 11 and AV50 shading dye) with a composition comprising Celluclean® and various control compositions.

FIG. 11 shows the superior whiteness performance over multiple washes of compositions comprising Cellulase SEQ ID NO: 11 compared to Celluclean®.

Figure 12:
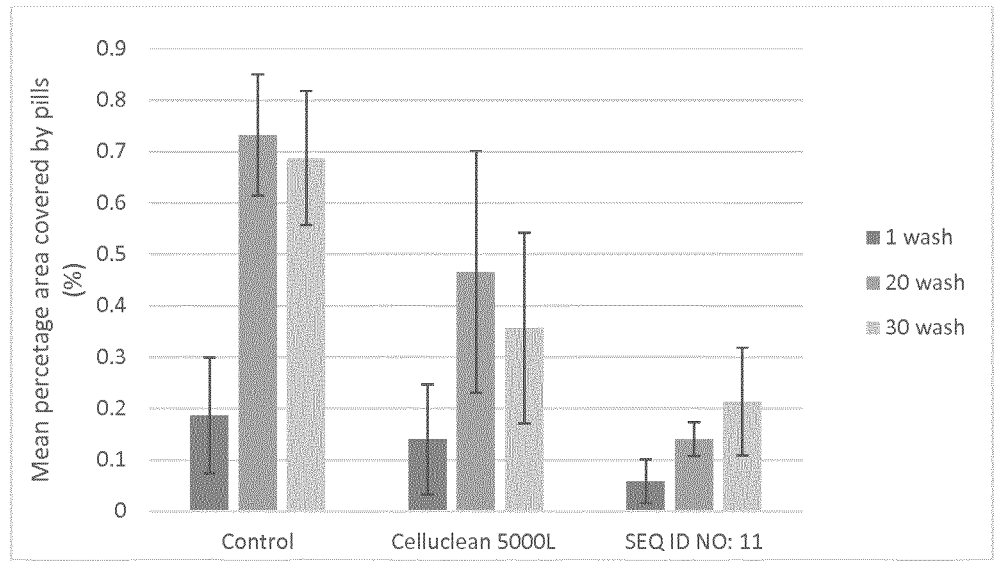

FIG. 12 shows the depilling effect of Cellulase SEQ ID NO: 11 is superior to that of Celluclean®.

Figure 13:
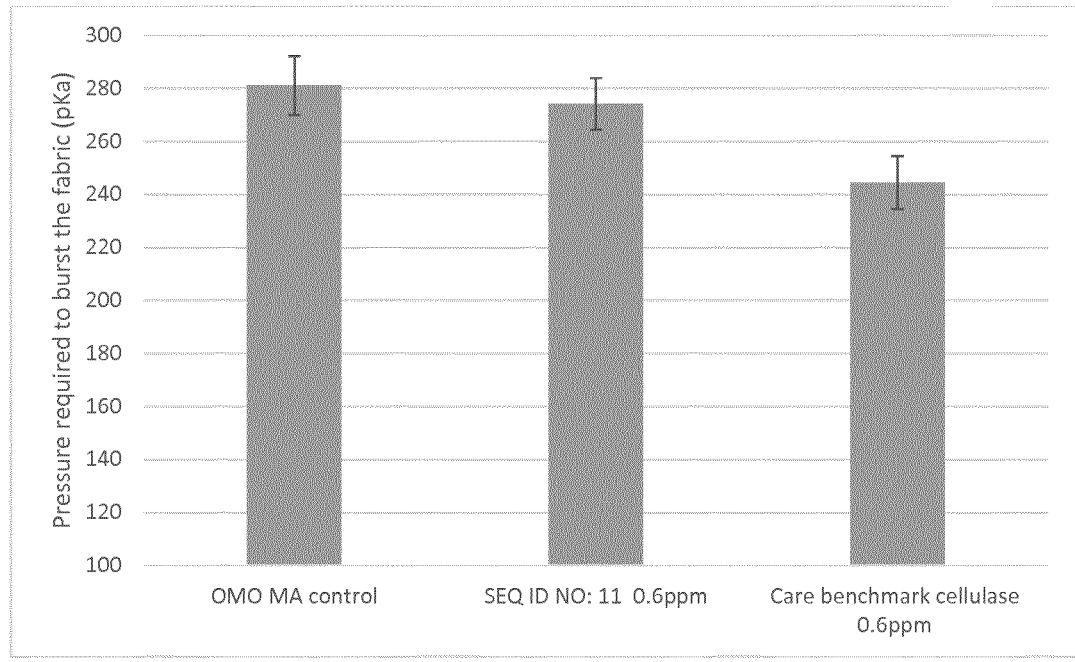

FIG. 13 shows the burst strength data for new drimarine blue fabric swatches washed 15 times with a control, a composition comprising Cellulase SEQ ID NO: 11 and a benchmark "Care" cellulase.

EXAMPLE 1

Cellulase Expression of Cellulases in *Pichia pastoris*

For the expression of the proteins (the following methods refers to SEQ ID NO: 15 and SEQ ID NO: 1 as examples), the corresponding genes (SEQ ID NO: 2 and SEQ ID NO: 16) were cloned into standard vectors at first. Therefore, the two genes were amplified via PCR with primers having a restriction site as overhang. PCR products and vectors (pGAPZα A, pPICZα A; Invitrogen™), digested with KpnI and XbaI, were ligated according to suppliers manual. The resulted vectors are listed in table 1.

TABLE 1

| Plasmid names and description | |
| --- | --- |
| plasmid name | description |
| pGAP-SEQ ID NO: 1 | pGAPZα A with SEQ ID NO: 1 |
| pAOX-SEQ ID NO: 1 | pPICZα A with SEQ ID NO: 1 |
| pGAP-SEQ ID NO: 15 | pGAPZα A with SEQ ID NO: 15 |
| pAOX-SEQ ID NO: 15 | pPICZα A with SEQ ID NO: 15 |

After linearization with BglI, the vectors were transformed into X-33 strain (Invitrogen™) according to suppliers manual. For each plasmid, 96 transformants were screened for high protein production in deep-well plates. From each transformant series the best 5-10 clones were cultivated in 300 ml shake flasks (50 ml YP base medium with 1% glycerol; 27° C., 250 rpm, 80% humidity; 2 ml shots of glycerin or methanol after 40 h, 48 h, 66 h and 72 h; harvest after 96 h) for verification. The activity of the proteins was determined with Azo-CMC Assay (Megazyme, Ireland) at the end.

EXAMPLE 2

Determination of Enzyme Concentration by Gel Quantification of Target Bands

SEQ ID NO: 1, SEQ ID NO: 11, SEQ ID NO: 13, SEQ ID NO: 15 and SEQ ID NO: 17 fermentation supernatants were quantified via an in house SDS gel quantification method using an external protein calibration curve. Enzyme samples were applied to an SDS gel which was subsequently stained with Sypro™ Ruby (Thermo Fisher™: S12000). The gel image was recorded on a standard Bio-Rad™ gel documentation instrument. Image analysis was performed using ImageLab software (Bio-Rad™). Protein concentration was determined by signal integration of the target protein's specific SDS gel band using the external protein calibration curve on the same SDS gel (e.g. BSA; bovine serum albumin).

EXAMPLE 3

Cellulase Quantification in Fermentation Supernatants Using Specific Enzyme Activities SEQ ID NO: 1 and SEQ ID NO: 11 were purified to homogeneity by Ni-NTA purification followed by size exclusion chromatography using a Superdex® 75 10/300GL column. The protein sequences were determined experimentally by intact mass determination and N-terminal sequencing. Protein quantification of the homogenous samples was performed by HPLC with UV280 signal detection using the molar extinction coefficient calculated from the experimentally determined protein sequence. In brief, HPLC runs were performed as follows. The protein was applied to an end capped Nucleosil® C4 column and eluted by a linear gradient of buffer A (90% water, 10% acetonitrile, 0.1% TFA) and buffer B (100% acetonitrile, 0.1% TFA). The peak UV280 signal was integrated to calculate the protein concentration. Volumetric enzyme activities of purified SEQ ID NO: 1 and SEQ ID NO: 11 samples, or crude protein supernatants were measured using a modified, 96 well enabled Cellazyme® C assay (Megazyme™). Specific and molar activities of size exclusion chromatography purified SEQ ID NO: 1 and SEQ ID NO: 11 were used to calculate target protein concentrations in the crude fermentation supernatants.

EXAMPLE 4

ARD (Anti-Re-Deposition) Wash Activity of Cellulases

The activity of cellulases was tested in an ARD washing test in Tergotometer scale. White cotton swatches (T460-40, center for testmaterials B.V. 3133 KT Vlaardingen, The Netherlands) were washed 4 times 20 minutes in 800 mL at 40° C. The wash liquor consisted of the detergent AATCC WOB 93 in a dosage of 1.5 g/L in water with a defined French hardness of 27, Ca:Mg 2:1. To each wash cycle 8 new cotton swatches soiled with carbon black and olive oil (8×10 cm; 101 swissatest Testmaterialien AG, 9015 St Gallen, Switzerland) were added as soil ballast. The liquor cloth ratio was set to 25 by adding cotton fabric 80 A and 10 A (wfk Testgewebe GmbH, 41379 Bruggen, Germany) as ballast. The L*a*b* values of the white cotton swatches were recorded after drying the textile at the air using a spectrophotometer with D65, 10° (ColorFlex® EZ, Hunterlab®). The instrument was calibrated prior to the measurement with a supplied white standard. The dL* value was calculated by subtraction of the L* of a blank control without enzyme from L* of cotton swatches treated with cellulase. The dL* reflects the whiteness of a fabric, a higher dL* therefore indicates a higher ARD-effect of enzyme. Enzymes were dosed as mg of active enzyme protein (AEP). AEP content of each preparation was calculated based on specific enzyme activities. The protein quantification was performed as described in example 3. Dosage of the enzyme preparations was 0.625 mg of active enzyme protein per liter of wash liquor and control sample contained no enzyme.

Figure 1:
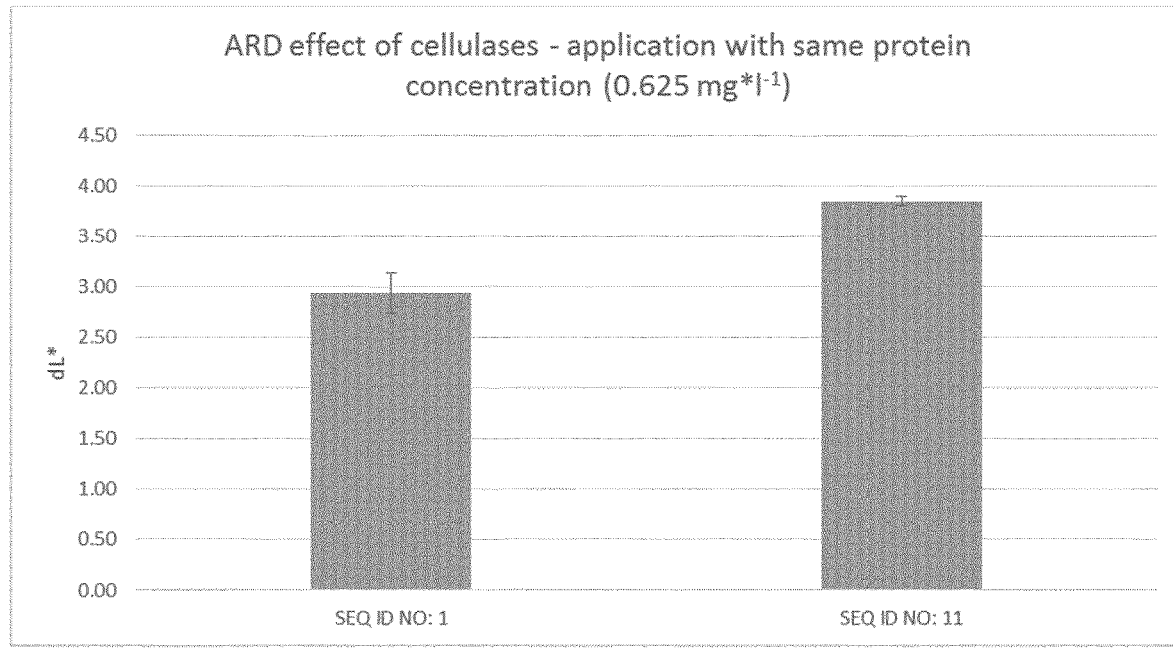
FIG. 1 shows the results of example 4: a comparison of the dL*-value of SEQ ID NO: 1 and SEQ ID NO: 11

Results are shown in FIG. 1. Applying the enzymes with the same protein concentration resulted in a higher dL* value for SEQ ID NO: 11 (3.85) compared to SEQ ID NO: 1 (2.94) indicating an increased ARD-effect for SEQ ID NO: 11.

EXAMPLE 5

ARD (Anti Re-Deposition) Wash Activity of Cellulase Variants

The activity of cellulases was tested in an ARD washing test in Tergotometer scale. White cotton swatches (T460-40, center for testmaterials B.V. 3133 KT Vlaardingen, The Netherlands) were washed 4 times 20 minutes in 800 mL at 40° C. The wash liquor consisted of detergent AATCC WOB 93 in a dosage of 1.5 g/L in water with set French hardness 27, Ca:Mg 2:1. To each wash cycle 8 new cotton swatches soiled with carbon black and olive oil (8×10 cm; 101 swissatest Testmaterialien AG, 9015 St Gallen, Switzerland) were added as soil ballast. The liquor cloth ratio was set to 25 by adding cotton fabric 80 A and 10 A (wfk Testgewebe GmbH, 41379 Bruggen, Germany) as ballast. The L*a*b* values of the white cotton swatches were recorded after drying the textile at the air using a spectrophotometer with D65, 10° (ColorFlex® EZ, Hunterlab®). The instrument was calibrated prior to the measurement with a supplied white standard. The dL* value was calculated by subtraction of the L* of a blank control without enzyme from L* of cotton swatches treated with cellulase. The dL* reflects the whiteness of a fabric, a higher dL* therefore indicates a higher ARD-effect of enzyme. Enzymes were dosed as mg of active enzyme protein (AEP). AEP content of each preparation was calculated based on a SDS-PAGE, which was applied for protein quantification (example 2). Dosage of the enzyme preparations was 1.5 mg of active enzyme protein per liter of wash liquor and control sample contained no enzyme.

Figure 2:
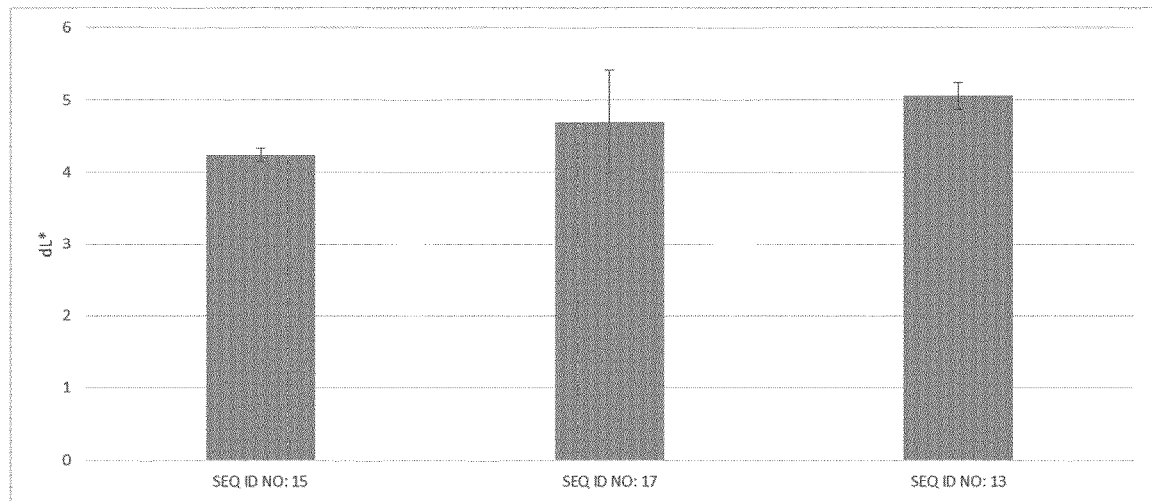
FIG. 2 shows the results of example 5: applying the different cellulose variants resulted in different L+-values, indicating different ARD-effect of the inventive celluloses SEQ ID NO: 15, SEQ ID NO: 13 and SEQ ID NO: 17.

Results are shown in FIG. 2. Applying the different cellulose variants resulted in different L+-values, indicating different ARD-effect of the cellulose variants.

EXAMPLE 6

ARD (Anti Re-Deposition) Wash Activity of Enzymes with Carpet Soil

The wash activity of cellulases was tested in an ARD washing test in Tergotometer scale. White cotton swatches (T460-40, center for testmaterials B.V. 3133 KT Vlaardingen, The Netherlands) were washed 7 times 20 minutes in 800 mL at 35° C. The wash liquor consisted of the detergent AATCCliqD in a dosage of 2 g/L in water with French hardness set to 26, Ca:Mg 2:1. Liquor cloth ratio was set to 29 by adding cotton fabric 80 A and 10 A (wfk Testgewebe GmbH, 41379 Bruggen, Germany) as ballast. As soil, 10 g/L carpet soil wfk 09 W (wfk Testgewebe GmbH, 41379, Bruggen, Germany) was added into the wash liquor at each wash cycle.

Enzymes were dosed in a concentration of 0.625 mg/L (AEP; active protein; example 2). The L*a*b* values of the white cotton swatches were recorded after drying the textile at the air using a spectrophotometer with D65, 10° (Color-Flex® EZ, Hunterlab®). The instrument was calibrated daily prior to each measurement with the supplied white standard (Hunterlab®). The dL* value was calculated by subtraction of the L* of a blank control without enzyme from L* of cotton swatches treated with cellulase. The dL* gives the whiteness of a fabric, a higher dL* therefore indicates a higher ARD-effect of enzyme.

Results are shown in FIG. 3. SEQ ID NO: 11 shows a positive ARD effect with dL* of ~2 compared to fabric washed without enzyme treatment. Celluclean® 5000 L on the other hand and shows on average a minimal negative ARD wash effect with carpet soil.

EXAMPLE 7

Launder-O-Meter Tests of a Cellulase with Liquid Detergent Application

The tests were conducted as disclosed in WO 2016 066896. The cellulase (SEQ ID NO: 11) was produced in *Pichia pastoris*, as described in example 1, and tested for their performance with AATCCliq. detergent at 40° C. The monitor E-253 was used for the demonstration of the de-pilling effect representing used cotton textiles. The test fabrics were cut into swatches (approx. 29 cm×15-16.5 cm, total weight of two swatches approx. 24 g) containing full width stripes of each color (black, red, green, blue). Cellulase treatments were performed in an Atlas LP-2 Launder-Ometer® (SDL Atlas, Rock Hill, S.C. 29732, USA) as follows. The Launder-Ometer® was first pre-heated to 40° C. Subsequently, 60 g of steel balls (diameter 0.6 cm) and 240 ml of wash liquor and diluted enzyme (<1.0 ml) were added into 1.2 liter containers. After that, one swatch of E-253 was placed in containers and the Launder-Ometer® was run at 40° C. for 60 min.

Enzymes were dosed as mg of active enzyme protein (AEP). AEP content of each preparation was calculated based on a SDS-PAGE which was applied for protein quantification (example 2).

Dosage of the enzyme preparations was 0.4 mg of active enzyme protein per liter of wash liquor and control sample contained no enzyme. The wash liquor contained 5 g of AATCCliq. per litre of synthetic tap water (16° dH). The preparation of the synthetic tap water with a hardness of 16° dH was prepared as described in WO 2016 066896 in example 4. After the cellulase treatment in the Launder-Ometer®, the swatches were first rinsed separately under running water (ambient temperature ~20° C.) and then dried in a spin-dryer (THOMAS, Neunkirchen; Type: 776 SEL 202) for 5 minutes.

The cellulase performance in detergent application was evaluated by measuring the color of as reflectance values using a spectrophotometer (ColorFlex® EZ, Hunterlab®) using La*b* color space coordinates. The color of each 4 stripes of test monitors was measured after 5 washing cycles. Decrease of lightness (L*), i.e. increase of darkness compared to treatment without cellulase, was used as an indication of cellulase effect. When the surface fibers and fibrils protruding from the yarn forming pills and giving the fabric a greyish look are removed by cellulase, the lightness of the fabric decreases, and the surface of the fabric appears darker and colors get brighter (WO 2016 066896).

Cellulase performance was calculated according to WO 2016 066896 in example 4. The sum of the L*-values of all 4 test strips on the monitor appeared to be negative (−2.50). As described above, a negative L*-value indicates the removal of fibers and fibrils protruding from the yarn forming pills, giving the fabric a greyish look. The spectrophotometrical results were also confirmed by visual evaluation.

EXAMPLE 8

ARD (Anti-Re-Deposition) Wash Activity of a Cellulase at 20° C.

The activity of SEQ ID NO: 11 was tested in an ARD washing test in Tergotometer scale at 20° C. White cotton swatches (WK05, wfk Testgewebe GmbH, 41379 Brüggen, Germany) were washed 20 minutes in 800 mL at 20° C. The wash liquor consisted of the detergent IKEA12 in a dosage of 0.72 g/L in water with a defined French hardness of 26, Ca:Mg 2:1. To each wash cycle 0.04 g/L were added.

The IKEA formulation is:

| Ingredient | Wt. % |
| --- | --- |
| Demin water | To 100 |
| TEA | 1.95 |
| NaOH | 1.28 |
| Gulf Farabi ™ LAS (linear alkylbenzene sulfonate) | 11.33 |
| Texapon ® N701 (1EO) (nonionic surfactant) | 7.17 |
| Proxel ® GXL (1,2-benzisothiazolin-3-one) | 0.02 |
| Neolone ™ 950 (Methylisothiazolone) | 0.01 |
| NaCl | 1.00 |

The liquor cloth ratio was set to 33 by adding a woven cotton fabric as ballast. The L*a*b* values of the white cotton swatches were recorded after drying the textile at 25° C.; 10% humidity overnight in a spectrophotometer with D65, 10° (ColorFlex® EZ, Hunterlab®). The instrument was calibrated prior to the measurement with a supplied white standard. The dL* value was calculated by subtraction of the L* of a blank control without enzyme from L* of cotton swatches treated with cellulase. The dL* reflects the whiteness of a fabric, a higher dL* therefore indicates a higher ARD-effect of enzyme. Enzymes were dosed as mg of active enzyme protein (AEP). AEP content of each preparation was calculated based on the method described in example 2. Dosage of the enzyme preparations was 0.625 mg of active enzyme protein per liter of wash liquor and control sample contained no enzyme.

Results are shown in FIG. 4. Applying SEQ ID NO: 15 with a concentration of 0.625 mg/L resulted in a dL* value of 4.5.

EXAMPLE 9

Determination of Temperature Optimum of SEQ ID NO: 11

For the determination of the temperature optimum 100 µL enzyme solutions in 100 mM sodium acetate buffer pH 5 were mixed with 100 μL 1% aqueous carboxymethyl-cellulose solution and incubated for 10 minutes at 10° C., 20° C., 30° C., 40° C., 50° C., 60° C., 70° C., 80° C., 90° C. and 99° C., shaking. The reactions were stopped by incubation of the reaction mixes at 95° C. for 5 minutes. Activity was determined by measurement of the liberated reducing ends using the p-hydroxybenz-hydrazide assay.

For reducing end determination, a 5% (w/v) p-hydroxybenz-hydrazide stock solution in 0.5 M HCl was diluted 1:3 in 0.5 M NaOH to yield the p-hydroxybenz-hydrazide working solution. 50 μL of sample was mixed with 150 μL of working solution and the reaction was incubated for 5 min at 95° C. After cooling to 4° C. the absorbance at 410 nm was determined and liberated reducing ends were calculated using a glucose calibration curve.

The results show (FIG. 5), that SEQ ID NO: 11 guarantees activity at all temperatures relevant for cleaning and washing applications. Even at low temperatures an activity of more than 20% is maintained.

EXAMPLE 10

Determination of pH Optimum of SEQ ID NO: 11

For the determination of pH optimum, an enzyme stock solution was diluted in 120 mM Britton-Robinson universal buffers adjusted to pH 2, 3, 4, 5, 6, 7, 8, 9, 10, 11 and 12, respectively. 100 μL of these dilutions were mixed with 100 μL aqueous 1% carboxymethyl-cellulose solution and incubated for 10 minutes at 70° C., shaking. The reactions were stopped by incubation of the reaction mixes at 95° C. for 5 minutes. Activity was determined by measurement of the liberated reducing ends using the p-hydroxybenz-hydrazide assay as described in Example 9.

The results show (FIG. 6) that SEQ ID NO: 11 guarantees activity over a broad pH range and still shows very good activity at high/basic pH values (up to pH 9) which are relevant for washing and cleaning applications.

EXAMPLE 11

Determination of Temperature and pH Optimum, and Thermostability of SEQ ID NO: 11

For the determination of temperature stability 100 μL enzyme solutions in 100 mM sodium acetate buffer pH 5 were incubated for 30 min at 10° C., 20° C., 30° C., 40° C., 50° C., 60° C., 70° C., 80° C., 90° C. and 99° C. Solutions were cooled to 4° C. Subsequently, 100 μL of aqueous 1% carboxymethyl-cellulose solution were added and the samples were incubated at 50° C. for 10 minutes. The reactions were stopped by addition of 40 μL 1 M sodium carbonate solution. Activity was determined by measurement of the liberated reducing ends using the p-hydroxybenz-hydrazide assay as described in Example 9.

The results show (FIG. 7) that SEQ ID NO: 11 guarantees excellent temperature stability showing activity for a broad temperature range.

EXAMPLES 12 TO 17

Methods and materials used: —
Tergotometer Wash Studies
The conditions used in the wash process were as follows:
Temperature: 20 degrees Celsius or 45 degrees Celsius
Enzyme concentration: 0.625 ppm
Product dose: 0.72 gpl IKEA or RIN powder
Soil dose: 0.04 gpl carbon black
Shading dye dose: 0.006% AV50
Wash time: 1×20 minute wash
Rinse time: 1×10 seconds rinse
The IKEA liquid formulation used was:

| Ingredient | Wt. % |
| --- | --- |
| Demin water | To 100 |
| TEA | 1.95 |
| NaOH | 1.28 |
| Gulf Farabi ™ LAS (linear alkylbenzene sulfonate) | 11.33 |
| Texapon ® N701 (1EO) (nonionic surfactant) | 7.17 |
| Proxel ® GXL (1,2-benzisothiazolin-3-one) | 0.02 |
| Neolone ™ 950 (Methylisothiazolone) | 0.01 |
| NaCl | 1.00 |

The RIN powder formulation used was:

| Ingredient | RIN powder Wt. % |
| --- | --- |
| Sodium LAS (linear alkylbenzene sulfonate) | 12.00 |
| Methyl Ether Sulfonate | 3.00 |
| Soda Ash | 24.00 |
| Calcite (Calcium carbonate) | 10.00 |
| Dolomite (Calcium magnesium carbonate) | 5.00 |
| Sodium Chloride | 39.00 |
| Sodium Sulphate | 3.00 |
| Minors & Moisture | To 100% |

The OMO formulations used are:

| Ingredient | OMO low active Wt. % | OMO high active Wt. % |
| --- | --- | --- |
| Sodium LAS (linear alkylbenzene sulfonate) | 8.00 | 15.00 |
| Sodium Silicate | 7.11 | 7.5 |
| Soda Ash | 22.89 | 17.4 |
| Sodium Sulphate | 59.39 | 56.9125 |
| Sokalan ® CP5 (Copolymer of acrylic acid and maleic acid) | 0.36 | 0.2625 |
| S.C.M.C (Sodium carboxymethylcellulose) | 0.13 | 0.16875 |
| Tinopal ® CBSx/DSBP (Flourescer) | 0.02 | 0.0225 |
| Moisture | 1.78 | 2.25 |
| Salts | 0.28 | 0.48 |

Multiple Machine Wash Studies
Cotton Monitors used were pre aged by washing them 20 times with OMO powder. 3 replicates per wash point of 1, 3, 5, 10, 15, 20, 25 and 30 washes were used. Soil Monitors used comprised of 3×E101 monitors. Fabrics were washed in a range of formulations+/−Celluclean® and AV50 (shading dye) to assess if there is any improvement to redeposition due to the enzyme being present. Machines used for the study were Asian TLA 45 L. Washes were carried out in 40° C. 26 FH (2:1 Ca:Mg) 45 L wash liquor and the ballast load used was 1.5 kg.

Fabric Pill Removal Assessment
Pill removal via cellulases was assessed using the instrumental pilling measurement equipment. Fabrics washed with the various cellulase technologies were analysed by taking multiple images and the subsequent images were then processed to give a percentage area covered by pills.

Burst Strength Analysis

The TruBurst™-Intelligent Bursting Strength Tester is a computer-controlled pneumatic testing device. It is used to perform bursting strength tests on a variety of textile substrates including woven, knitted and non-woven fabrics when standard tensile strength methods are unsuitable.

Except in special cases (for example wet tests), physical and mechanical testing of textiles are carried out in the conditioned state in the standard temperature atmosphere and relative humidity as given by ISO 139 standard. The standard temperature atmosphere is 20° C. and 65% relative humidity.

Drimarene blue interlocked cotton fabrics washed 15 times with the different enzyme technologies were cut in half to open up the fabric. 12 measurements per swatch were then taken using the conditions outlined below:

Temperature: 20° C.

Relative Humidity: 65%

Weight: 0

NTests: 3/3

Diaphragm: 1.0 mm

Test area: 50 cm$^2$ (79.8 mm Dia)

Inflation Rate: 15 kPa/s

Correction Rate: 3 kPa/s

Burst Detect: Normal

Clamp Pressure: 500 kPa

Target Pressure: OkPa

Target Distance: 0.0 mm

EXAMPLE 12

This example shows that Cellulase SEQ ID NO: 11 outperforms Celluclean® with regard to whiteness benefit (FIG. 8). The Cellulase SEQ ID NO: 11 provided a statistically significant improvement in terms of whiteness in comparison to Celluclean®. The test method used was the tergotometer wash studies as described earlier @ 45° C. and used the RIN powder.

|  | Control (RIN powder) | Cellulase SEQ ID NO: 11 | Celluclean ® |
| --- | --- | --- | --- |
| mean L* | 68.76 | 73.46 | 70.51 |
| stdev | 1.09 | 1.19 | 1.04 |
| 95% CI | 0.68 | 0.74 | 0.65 |

EXAMPLE 13

This example also shows that Cellulase SEQ ID NO: 11 outperforms Celluclean® with regard to whiteness benefit (FIG. 9). This example was carried out at different washing temperatures (20 and 45 degrees Celsius). The Cellulase SEQ ID NO: 11 provided a statistically significant improvement in terms of whiteness in comparison to Celluclean®. Test method was the tergotometer wash studies described earlier @ both 20° C. and 45° C. using the IKEA liquid formulation.

At 20 Degrees Celsius

|  | Control (IKEA formulation) | Cellulase SEQ ID NO: 11 | Celluclean ® |
| --- | --- | --- | --- |
| mean L* | 75.23 | 80.77 | 77.07 |
| stdev | 1.16 | 0.99 | 1.84 |
| 95% CI | 0.72 | 0.61 | 1.14 |

At 45 Degrees Celsius

|  | Control (IKEA formulation) | Cellulase SEQ ID NO: 11 | Celluclean ® |
| --- | --- | --- | --- |
| mean L* | 71.33 | 78.83 | 77.20 |
| stdev | 1.39 | 1.02 | 1.00 |
| 95% CI | 0.86 | 0.63 | 0.62 |

EXAMPLE 14

This example shows that the combination of Cellulase SEQ ID NO: 11 with a shading dye (AV50) provides a synergistic effect in terms of whiteness over and above the effects provided individually by the Cellulase SEQ ID NO: 11 and shading dye (FIG. 10). The whiteness values (dL*) are stated as the difference over the control formulation (IKEA liquid) without shading dye or cellulase. The test method used was the tergotometer wash studies as described earlier @ 20° C.

|  | Whiteness value (dL*) (normalized versus base formulation - IKEA liquid) |
| --- | --- |
| +Shading Dye (AV50) | 1.9 ± 0.3 |
| +Celluclean ® | 2.6 ± 0.3 |
| +Cellulase SEQ ID NO: 11 | 3.4 ± 0.3 |
| +AV50 + Celluclean ® (Calculated) | 4.5 ± 0.2 |
| +AV50 + Celluclean ® (Measured) | 4.0 ± 0.4 |
| +AV50 + Cellulase SEQ ID NO: 11 (Calculated) | 5.3 ± 0.2 |
| +AV50 + Cellulase SEQ ID NO: 11 (Measured) | 7.2 ± 0.3 |

It is notable that the combination of Cellulase SEQ ID NO: 11 with a shading dye (AV50) provides a synergistic benefit (measured versus calculated), in comparison to the Celluclean® combination with shading dye, where the measured value is lower than the calculated whiteness value.

EXAMPLE 15

This example shows that the enhanced whiteness effect persisted over many (30) washes for Cellulase SEQ ID NO: 11 in comparison to Celluclean®. The effect was shown on knitted aged cotton and the base formulation was commercially available OMO powder. The values shown at M60 Reflectance values normalised from unwashed fabric, so they are given as negative values. A smaller negative value means the washed fabric is closer to pristine unwashed value. FIG. 11 shows some selected results (for OMO, OMO+Celluclean®, and OMO+Cellulase SEQ ID NO: 11) from the table below in graphical format. The test method was the multiple machine wash studies method as described earlier.

| | OMO | OMO + AV50 | OMO + Cellu- clean® | OMO + Cellulase SEQ ID NO: 11 | OMO + Cellu- clean® + AV50 | OMO + Cellulase SEQ ID NO: 11 + AV50 |
|---|---|---|---|---|---|---|
| 1 Wash | −8.4 | −7.9 | −4.8 | −5.2 | −6.4 | −7.2 |
| 3 W | −13.6 | −13.5 | −7.3 | −6.9 | −8.8 | −8.0 |
| 5 W | −15.1 | −16.3 | −9.9 | −8.9 | −10.9 | −9.6 |
| 10 W | −21.4 | −21.7 | −19.2 | −15.1 | −19.8 | −15.3 |
| 15 W | −23.6 | −23.7 | −19.0 | −15.9 | −20.6 | −16.3 |
| 20 W | −25.1 | −24.1 | −19.2 | −17.2 | −19.9 | −16.8 |
| 25 W | −25.4 | −25.1 | −20.0 | −17.4 | −19.9 | −17.8 |
| 30 W | −26.6 | −26.8 | −21.3 | −19.1 | −20.5 | −18.2 |

EXAMPLE 16

This example shown in (FIG. 12) shows that Cellulase SEQ ID NO: 11 also outperforms Celluclean® (the reference) with respect to fabric care, specifically de-pilling. This experiment was carried out with commercially available OMO powder. The measured value was the mean percentage area covered by pills. A lower number is better as it means fewer pills on the fabric. The test was the fabric pill removal assessment as defined earlier.

| | Control (OMO powder) | Control + Reference (Celluclean®) | Control + Cellulase SEQ ID NO: 11 |
|---|---|---|---|
| 1 wash | 0.19 (0.11 st. dev) | 0.14 (0.11 st. dev) | 0.06 (0.04 st. dev) |
| 20 wash | 0.73 (0.12 st. dev) | 0.47 (0.24 st. dev) | 0.14 (0.03 st. dev) |
| 30 wash | 0.69 (0.13 st. dev) | 0.36 (0.19 st. dev) | 0.21 (0.11 st. dev) |

EXAMPLE 17

Importantly, this de-pilling is accompanied by comparatively little loss in tensile strength as seen in the burst strength data (see FIG. 13), which is advantageous as some vigorous "care" enzymes efficiently remove pills, but weaken fabric, curtailing the garment's wearable lifespan. This example shows that there is extended thermo resistance as measured by burst strength shown by the Cellulase SEQ ID NO: 11 versus the Celluclean® reference. The fabric was washed 15 times and the control was commercially available OMO powder. The method used the burst strength analysis method as defined earlier.

| | Control (OMO powder) | Control + Cellulase SEQ ID NO: 11 | Control + Reference (Celluclean®) |
|---|---|---|---|
| Mean Pressure (pKa) | 281.1 | 274.1 | 244.4 |
| Standard Deviation (st. dev) | 11.1 | 9.7 | 10.0 |

Sequences identified within the present invention:
SEQ ID NO: 1 sequence comprising a catalytic domain motive [STA]-T-R-Y-[FYW]-D-x(5)-[CA]
SEQ ID NO: 2 corresponding nucleotide sequence to SEQ ID NO: 1
SEQ ID NO: 3 carbohydrate binding domain
SEQ ID NO: 4 corresponding nucleotide sequence to SEQ ID NO: 3
SEQ ID NO: 5 linker sequence
SEQ ID NO: 6 corresponding nucleotide sequence to SEQ ID NO: 5
SEQ ID NO: 7 linker sequence
SEQ ID NO: 8 corresponding nucleotide sequence to SEQ ID NO: 7
SEQ ID NO: 9 preferred catalytic domain motive T-T-R—Y-W-D-C-C-K-P-S-C
SEQ ID NO: 10 corresponding nucleotide sequence to SEQ ID NO: 9
SEQ ID NO: 11 preferred cellulase according to the present invention
SEQ ID NO: 12 corresponding nucleotide sequence to SEQ ID NO: 11
SEQ ID NO: 13 preferred cellulase according to the present invention
SEQ ID NO: 14 corresponding nucleotide sequence to SEQ ID NO: 13
SEQ ID NO: 15 preferred cellulase according to the present invention
SEQ ID NO: 16 corresponding nucleotide sequence to SEQ ID NO: 15
SEQ ID NO: 17 preferred cellulase according to the present invention
SEQ ID NO: 18 corresponding nucleotide sequence to SEQ ID NO: 17
SEQ ID NO: 19 preferred carbohydrate binding domain tag
SEQ ID NO: 20 corresponding nucleotide sequence to SEQ ID NO: 19
SEQ ID NO: 21 to 24 are further sequences identified in the invention

The invention claimed is:

1. A detergent composition comprising:
   (a) a shading dye from 0.0001 to 1 wt. %; and
   (b) a cellulase having an amino acid sequence with at least 87% sequence identity to SEQ ID NO: 11.

2. The detergent composition according to claim 1, wherein the shading dye is a blue or violet shading dye.

3. The detergent composition according to claim 1, wherein the shading dye is a reactive dye covalently bound to a polymer, optionally wherein the polymer is a polyimine, or a polyimine substituted with 2-hydroxypropan-1-yl groups.

4. The detergent composition of claim 3, wherein the shading dye comprises a chromophore of formula:

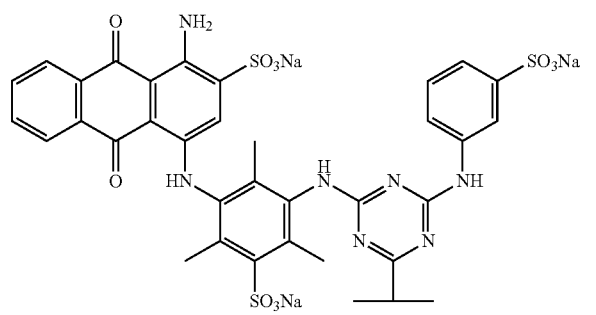

wherein ---- represents a point of attachment.

5. The detergent composition according to any of claim 1, wherein the dye is a direct dye, optionally wherein the direct dye is an azine dye, or has the following structure:

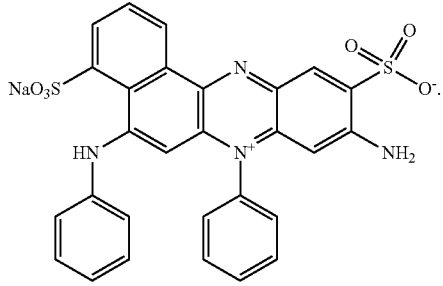

6. The detergent composition according to claim 1, wherein the composition comprises the shading dye from 0.0005 to 0.01 wt. %, and the cellulase from 0.001 to 5 wt. %.

7. The detergent composition according to claim 1, wherein the composition further comprises from a surfactant from 0.1 to 80 wt. %, optionally wherein the surfactant is an anionic surfactant, linear alkyl benzene sulphonates, alkyl sulphates, alkyl ether sulphates, or a mixture thereof.

8. A method of laundering white fabric, the method comprising contacting the fabric with an aqueous solution comprising the detergent according to claim 1, optionally wherein the step of contacting the fabric with the aqueous solution occurs at 30° C. or less.

* * * * *